(12) United States Patent
Karin et al.

(10) Patent No.: US 8,658,375 B2
(45) Date of Patent: Feb. 25, 2014

(54) COMPOSITIONS AND METHODS FOR DIAGNOSING AND TREATING AN INFLAMMATION

(75) Inventors: Nathan Karin, Haifa (IL); Gizi Wildbaum, Kiryat Yam (IL); Rachel Anunu, Haifa (IL); Yaniv Zohar, Kiryat-Haim (IL); Nir Netzer, Mazkeret Batia (IL)

(73) Assignee: Rappaport Family Institue for Research in the Medical Sciences, Haifa (IL)

( * ) Notice: Subject to any disclaimer, the term of this patent is extended or adjusted under 35 U.S.C. 154(b) by 0 days.

(21) Appl. No.: 13/205,668

(22) Filed: Aug. 9, 2011

(65) Prior Publication Data
US 2011/0287457 A1 Nov. 24, 2011

Related U.S. Application Data

(63) Continuation of application No. 11/222,745, filed on Sep. 12, 2005, now Pat. No. 8,017,113, which is a continuation-in-part of application No. PCT/IL2004/000241, filed on Mar. 14, 2004.

(60) Provisional application No. 60/453,512, filed on Mar. 12, 2003, provisional application No. 60/453,514, filed on Mar. 12, 2003.

(51) Int. Cl.
*G01N 33/53* (2006.01)

(52) U.S. Cl.
USPC .......................................................... 435/7.1

(58) Field of Classification Search
None
See application file for complete search history.

(56) References Cited

U.S. PATENT DOCUMENTS

| | | | |
|---|---|---|---|
| 5,459,128 | A | 10/1995 | Rollins et al. |
| 5,888,511 | A | 3/1999 | Skurkovich et al. |
| 6,087,385 | A | 7/2000 | Pershadsingh et al. |
| 6,316,420 | B1 | 11/2001 | Karin et al. |
| 6,420,346 | B1 | 7/2002 | Karin |
| 6,429,289 | B1 | 8/2002 | Krieger et al. |
| 7,245,748 | B2 | 7/2007 | Degani et al. |
| 7,345,910 | B2 | 3/2008 | Tsukamoto et al. |
| 7,417,037 | B2 | 8/2008 | Harty |
| 7,465,444 | B2 | 12/2008 | Watanabe |
| 7,749,714 | B2 | 7/2010 | Karin |
| 8,017,113 | B2 | 9/2011 | Karin |
| 2002/0086483 | A1 | 7/2002 | Kim et al. |
| 2002/0090379 | A1 | 7/2002 | Mouritsen et al. |
| 2004/0047861 | A1 | 3/2004 | Kehrel et al. |
| 2004/0052790 | A1 | 3/2004 | Skurkovich et al. |
| 2004/0086483 | A1 | 5/2004 | Karin |
| 2006/0035834 | A1 | 2/2006 | Karin |
| 2006/0193863 | A1 | 8/2006 | Karin |
| 2011/0287030 | A1 | 11/2011 | Karin et al. |
| 2013/0095119 | A1 | 4/2013 | Karin et al. |
| 2013/0259874 | A1 | 10/2013 | Karin et al. |

FOREIGN PATENT DOCUMENTS

| | | |
|---|---|---|
| EP | 1411848 | 4/2004 |
| EP | 1601374 | 12/2005 |
| EP | 1601682 | 12/2005 |
| EP | 1924605 | 1/2010 |
| WO | WO 95/05600 | 2/1995 |
| WO | WO 96/00288 | 1/1996 |
| WO | WO 99/11288 | 3/1999 |
| WO | WO 00/06203 | 2/2000 |
| WO | WO 01/57056 | 8/2001 |
| WO | WO 01/89565 | 11/2001 |
| WO | WO 02/16549 | 2/2002 |
| WO | WO 03/002009 | 1/2003 |
| WO | WO 2004/016769 | 2/2004 |
| WO | WO 2004/041179 | 5/2004 |
| WO | WO 2004/080273 | 9/2004 |
| WO | WO 2004/080385 | 9/2004 |
| WO | WO 2005/025613 | 3/2005 |
| WO | WO 2007/031996 | 3/2007 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994. 491-495.*
Colman et al. 'Effects of amino acid sequence changes on antibody-antigen interactions.' Research in Immunology. 145(1):33-36, 1994.*
Abaza et al. 'Effects of amino acid substitutions outside an antigenic site on protein binding to monoclonal antibodies of predetermined specificity obtained by peptide immunization: demonstration with region 94-100 (antigenic site 3) of myoglobin. Journal of Protein Chemistry.' 11(5):433-444, 1992.*
Lederman et al. °A single amino acid substitution in a common African allele of the CD4 molecule ablates binding of the monoclonal antibody, OKT4.' Molecular Immunology. 28:1171-1181, 1991.*
Chen et al. 'Anti-class a scavenger receptor autoantibodies from systemic lupus erythematosus patients impair phagocytic clearance of apoptotic cells by macrophages in vitro.' Arth. Res. Ther. 13:R1-9, 2011.*
Barter et al. "HDL Cholesterol, Very Low Levels of LDL Cholesterol, and Cardiovascular Events", The New England Journal of Medicine, 357(13): 1301-1310, Sep. 27, 2007.
Bocharov et al. "Synthetic Amphipathic Alpha-Helical Peptides, Mimics of Exchangeable Apolipoproteins, Block LPS Uptake and the Lipopolysaccharide-Induced Proinflammatory Cytokine Response in THP-1 Monocyte Cells", Circulation, Supplement II, 106(19): II-84, Abstract 425, Nov. 5, 2002.

(Continued)

*Primary Examiner* — Nora Rooney

(57) ABSTRACT

A method of reducing an inflammatory response in a subject is provided. The method comprising providing to a subject in need thereof a therapeutically effective amount of an agent capable of reducing activity and/or expression of a scavenger receptor or of an effector thereof, thereby reducing the inflammatory response in the subject.

8 Claims, 12 Drawing Sheets
(7 of 12 Drawing Sheet(s) Filed in Color)

(56) References Cited

OTHER PUBLICATIONS

Bottazzi et al. "A Chemoattractant Expressed in Human Sarcoma Cells (Tumor-Derived Chemotactic Factor, TDCF) Is Identical to Monocyte Chemoattractant Protein-1/Monocyte Chemotactic and Activating Factor (MCP-1/MCAF)", International Journal of Cancer, 45: 795-797, 19 90.

Braciak et al. "Recombinant Adenovirus-mRANTES Gene Transfer Into B16 Mouse Melanoma Cells Reduces Tumorgenicity In Vivo", The FASEB Journal, 8(4): Abstract 1159, 1994.

Brennan et al. "Cytokines in Autoimmunity", Current Opinion in Immunology, 8(6): 872-877, 1996.

Cao et al. "Complete Regression of Established Murine Hepatocellular Carcinoma by In Vivo Tumor Necrosis Factor ? Gene Transfer", Gastroenterology, 112: 501-510, 1997.

Chetcuti et al. "Identification of Differentially Expressed Genes in Organ-Confined Prostate Cancer by Gene Expression Array", The Prostate, 47: 132-140, 2001. Fig.5, Table I.

Cho "The Genetics and Immunopathogenesis of Inflammatory Bowel Disease", Nature Reviews: Immunology, 8(6): 458-466, 2008.

Colozza et al. "Proliferative Markers as Prognostic and Predictive Tools in Early Breast Cancer: Where Are We Now?", Annals of Oncology, 16: 1723-1739, 2005.

Cruse et al. "Antibodies", Illustrated Dictionary of Immunology, CRC Press, p. 18-19, 1995.

Desbaillets et al. "Human Astrocytomas and Glioblastomas Express Monocyte Chemoattractant Protein-1 (MCP-1) In Vivo and In Vitro", International Journal of Cancer, 58: 240-247, 1994.

Dohi et al. "Hapten-Induced Colitis Is Associated With Colonic Patch Hypertrophy and T Helper Cell 2-Type Responses", Journal of Experimental Medicine, 189(8): 1169-1179, Apr. 19, 1999.

Feldmann et al. "Role of Cytokines in Rheumatoid", Annual Reviews in Immunology, 14: 397-440, 1996.

Gordon et al. "High-Density Lipoprotein Cholesterol and Cardiovascular Disease. Four Prospective American Studies", Circulation, 79: 8-15, 1989.

Graves et al. "Monocyte Chemotactic Proteins From Human Tumor Cells", Biochemical Pharmacology, 47(3): 333-337, 1991.

Hayashida et al. "Lectin-Like Oxidized LDL Receptor-1 (LOX-1) Supports Adhesion of Mononuclear Leukocytes and A Monocyte-Like Cell Line THP-1 Cells Under Static and Flow Conditions", FEBS Letters, 511(1-3): 133-138, 2002. Introduction, Abstract.

Imachi et al. "Expression of Human Scavenger Receptor B1 on and in Human Platelets", Arterisclerosis, Thrombosis, and Vascular Biology, 23(5): 898-904, May 1, 2003.

Imachi et al. "Reduction of CLA-1 Expression on Human Platelet in the Patients With Atherosclerotic Disease and Diabetes Mellitus", Bunshi Tonyobyogaku, 10: 47-51, Dec. 1999. ACS on STN, HCAPLUS, AN 2000:540461, Accession No. 134:176698, Aug. 8, 2000.

Janciauskiene et al. "C-Terminal of ?1-Antitrypsin Activates Human Monocytes to A Pro-Inflammatory State Through Interactions With the CD36 Scavenger Receptor and LDL Receptor", Atherosclerosis, 158(1): 41-51, 2001.

Jiang et al. "Post-Translational Modification of A Monocyte-Specific Chemoattractant Synthesized by Glioma, Osteosarcoma, and Vascular Smooth Muscle Cells", The Journal of Biological Chemistry, 265(30): 18318-18321, 1990.

Kasama et al. "Interleukin-10 Expression and Chemokine Regulation During the Evolution of Murine Type II Collagen-Induced Arthritis", Journal of Clinical Investigation, 95: 2868-2876, 1995.

Kawahito et al. "15-Deoxy-?12,14-PGJ2 Induces Synoviocyte Apoptosis and Suppresses Adjuvant-Induced Arthritis in Rats", Journal of Clinical Investigation, 106(2): 189-197, 2000.

Krajewska et al. "Expression of BAG-I Protein Correlates With Aggressive Behavior of Prostate Cancers", The Prostate, 66: 801-810, 2006.

Leonard "Plasma Chemokine and Chemokine-Autoantibody Complexes in Health and Disease", Methods: A Companion to Methods in Enzymology, 10: 150-157, 1996.

Leung et al. "Monocyte Chemoattractant Protein-1 Expression and Macrophage Infiltration in Gliomas", Acta Neuropathologica, 93: 518-527, 1997.

Lubberts et al. "Adenoviral Vector-Mediated Overexpression of IL-4 in the Knee Joint of Mice With Collagen-Induced Arthritis Prevents Cartilage Destruction", Journal of Immunology, 163: 4546-4556, 1999. Abstract.

Mazzucchelli et al. "Monocyte Chemoattractant Protein-1 Gene Expression in Prostatic Hyperplasia and Prostate Adenocarcinoma", American Journal of Pathology, 149(2): 501-509, 1996. Abstract.

Momoi et al. "Inhibition of Monocyte Chemoattractant Protein-1 Expression in Cytokine-Treated Human Lung Epithelial Cells by Thiazolidinedione", Chest, 120(4): 1293-1300, 2001. Abstract.

Moore et al. "Distinct CXC Chemokines Mediate Tumorigenicity of Prostate Cancer Cells", American Journal of Pathology, 154(5): 1503-1512, 1999.

Murao et al. "Thiazolidinedione Inhibits the Production of Monocyte Chemoattractant Protein-1 in Cytokine-Treated Human Vascular Endothelial Cells", FEBS Letters, 454(1-2): 27-30, 1999. Abstract.

Negus et al. "The Detection and Localization of Monocyte Chemoattractant Protein-1 (MCP-1) in Human Ovarian Cancer", Journal of Clinical Investigation, 95: 2391-2396, 1995.

Nesbit et al. "Low-Level Monocyte Chemoattractant Protein-1 Stimulation of Monocytes Leads to Tumor Formation in Nontumorigenic Melanoma Cells", The Journal of Immunology: 6483-6490, 2001.

Podgaec et al. "Endometriosis: An Inflammatory Disease With A Th2 Immune Response Component", Human Reproduction, 22(5): 1373-1379, 2007.

Rudikoff et al. "Single Amino Acid Substitution Altering Antigen-Binding Specificity", Proc. Natl. Acad. Sci. USA, 79(6): 1979-1983, 1982.

Scarselli et al. "The Human Scavenger Receptor Class B Type IIs A Novel Candidate Receptor for the Hepatitis C Virus", The EMBO Journal, 21(19): 5017-5025, 2002. p. 5020, r-h Col., Lines 35-56, p. 5023, 1-h Col., Lines 7-26.

Selvan et al. "Expression of Multiple Chemokine Genes by Human Mast Cells Leukemia", The Journal of Biological Chemistry, 269(19): 13893-13898, 1994.

Sriram et al. "Experimental Allergic Encephalomyelitis: A Misleading Model of Multiple Sclerosis", Annals of Neurology, 58(6): 939-945, Dec. 2005.

Sylvester et al. "Neutrophil Attractant Protein-1 and Monocyte Chemoattractant Protein-1 in Human Serum. Effects of Intravenous Lipopolysaccharide on Free Attractants, Specific IgG Autoantibodies and Immune Complexes", The Journal of Immunology, 151(6): 3292-3298, Sep. 15, 1993.

Tandon et al. "Anti-CD36 Antibodies in Thrombotic Thrombocytopenic Purpura", British Journal of Haematology, 88: 816-825, Dec. 1994.

Tang et al. "Expression of BAG-1 in Invasive Breast Carcinomas", Journal of Clinical Oncology, 17(6): 1710-1719, Jun. 1999.

Temel et al. "Scavenger Receptor Class B, Type I (SR-BI) Is the Major Route for the Delivery of High Density Lipoprotein Cholesterol to the Steroidgenic Pathway in Cultured Mouse Adrenocortical Cells", Proc. Natl. Acad. Sci. USA 94: 13600-13605, 1997. Abstract.

Turner et al. "BAG-1: A Novel Biomarker Predicting Long-Term Survival in Early-Stage Breast Cancer", Journal of Clinical Oncology, 19(4): 992-1000, Feb. 15, 2001.

Van der Laan et al. "Regulation and Functional Involvement of Macrophage Scavenger Receptor MARCO in Clearence of Bacteria In Vivo", The Journal of Immunology, XP002380142, 162(2): 939-947, 1999.

Wildbaum et al. "A Targeted DNA Vaccine Augments the Natural Immune Response to Self TNF-Alpha and Suppresses Ongoing Adjuvant Arthritis", Journal of Immunolgy, 165(10): 5860-5866, 2000. p. 5860, Claims 1-10.

Wildbaum et al. "Augmentation of Natural Immunity to A Proinflammatory Cytokine (TNF-Alpha) by Targeted DNA Vaccine Confers Long-Lasting Resistance to Experimental Autoimmune Encephalomyelitis", Gene Therapy, 6: 1128-1138, 1999.

(56) References Cited

OTHER PUBLICATIONS

Wirger et al. "Plasma Levels of Monocyte Chemoattractant Protein-1 (MCP-1) in Patients With Metastatic Urological Cancers", Urological Research, 25(1): 92, 1997. Abstract p. 3.4.
Yoshimura et al. "Production and Characterization of Mouse Monoclonal Antibodies Against Human Monocyte Chemoattractant Protein-1", The Journal of Immunology, 147(7): 2229-2233, 1991.
Youssef et al. "Long-Lasting Protective Immunity to Experimental Autoimmune Encephalomyelitis Following Vaccination With Naked DNA Encoding C-C Chemokines", The Journal of Immunology, p. 3870-3879, 1998.
Youssef et al. "Prevention of Experimental Autoimmune Encephalomyelitis by MIP-1 ? and MCP-1 Naked DNA", Journal of Autoimmunity, 13: 21-29, 1999.
Isik et al. "Monocyte Chemoattractant Protein-1 mRNA Expression in Hemangiomas and Vascular Malformations", Journal of Surgical Research, 61: 71-76, 1996.
Karin "Gene Therapy for T Cell-Mediated Autoimmunity: Teaching the Immune System How to Restrain Its Own Harmful Activities by Targeted DNA Vaccines", IMAJ Journal, 2(Suppl.): 63-68, 2000.
Rabinovitch "An Update on Cytokines in the Pathogenesis of Insulin-Dependent Diabetes Mellitus", Diabetes/Metabolism Reviews, 14: 129-151, 1998.
Notice of Allowance Dated Oct. 2, 2012 From the US Patent and Trademark Office Re. U.S. Appl. No. 13/205,665.
Official Action Dated Sep. 21, 2012 From the US Patent and Trademark Office Re.: U.S. Appl. No. 11/991,711.
Supplementary Notice of Allowance Dated Jun. 17, 2013 From the US Patent and Trademark Office Re. U.S. Appl. No. 11/991,711.
Supplementary Notice of Allowance Dated Jun. 21, 2013 From the US Patent and Trademark Office Re. U.S. Appl. No. 13/721,309.
Restriction Official Action Dated Sep. 12, 2013 From the US Patent and Trademark Office Re. U.S. Appl. No. 13/913,578.

\* cited by examiner

FIGs. 1A-D
1A.
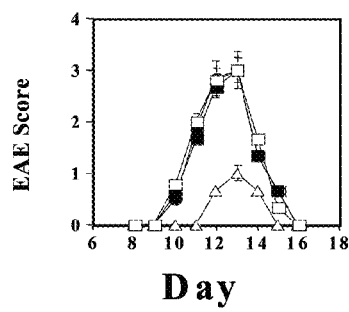
1B.
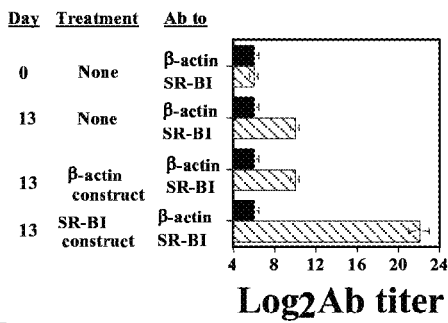
1C.
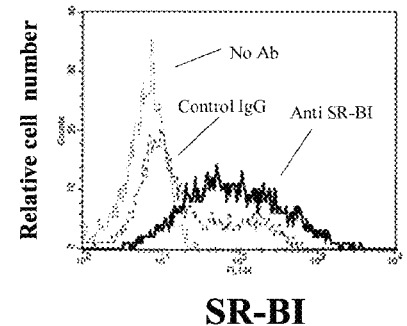
SR-BI
1D.
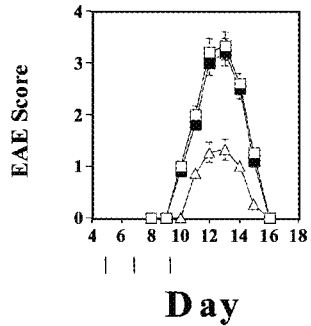
FIGs. 2A-C
2A.
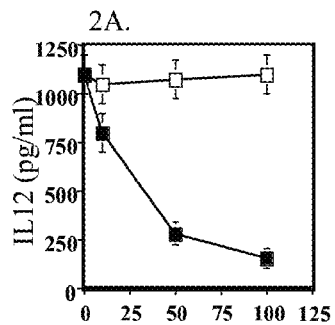
2B.
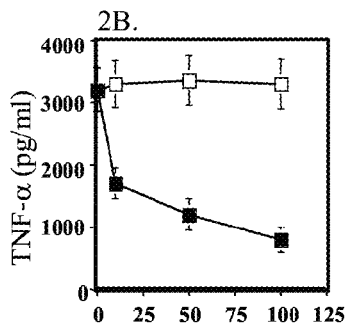
2C.
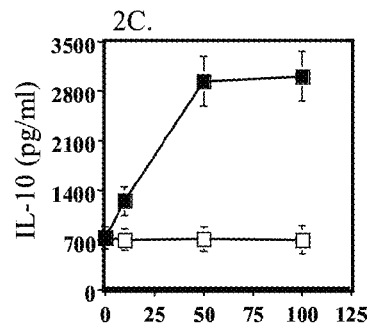
Anti SRB-I (µg/ml)

Normal colon

Control sick rat (colon)

Control IgG treated (colon)

Anti SRB-I therapy (colon)

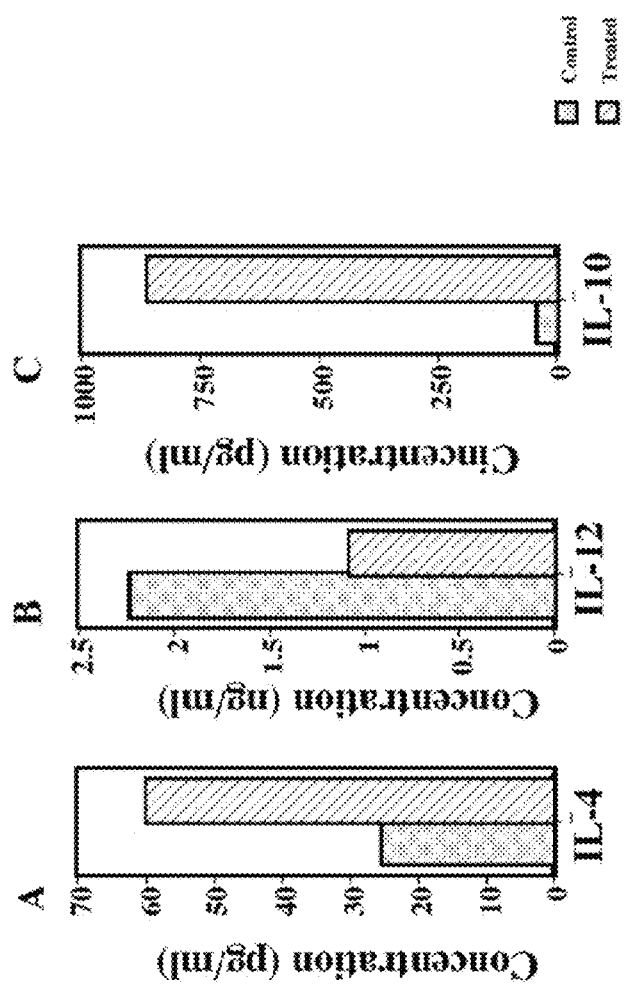
Figs. 10a-c

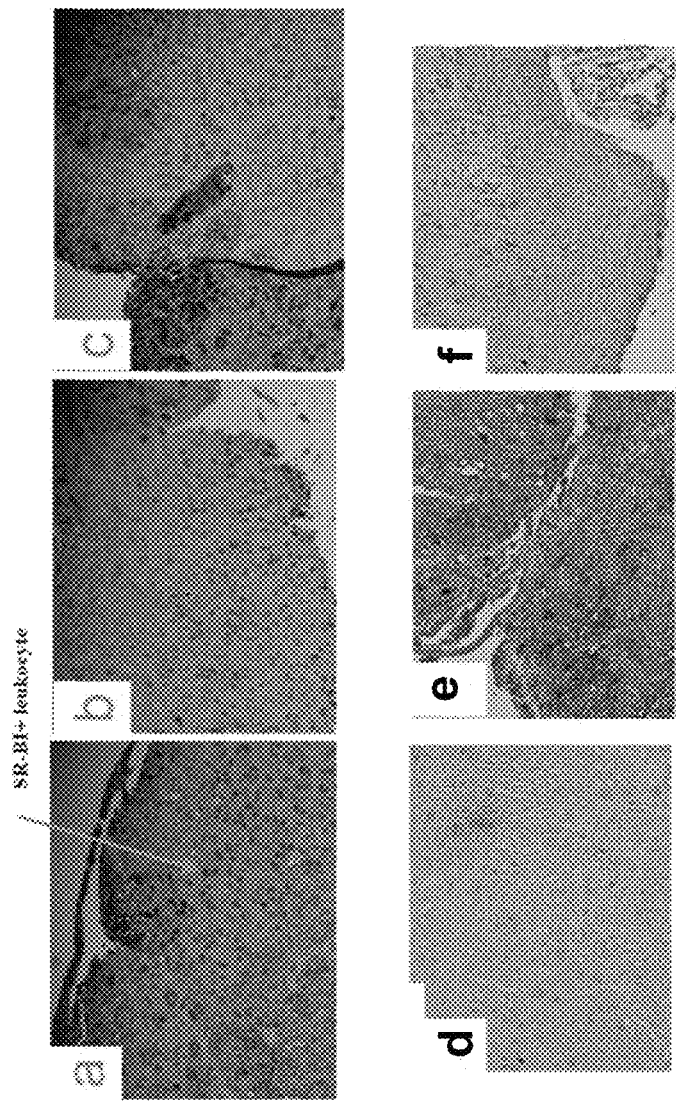
Figs. 11a-f

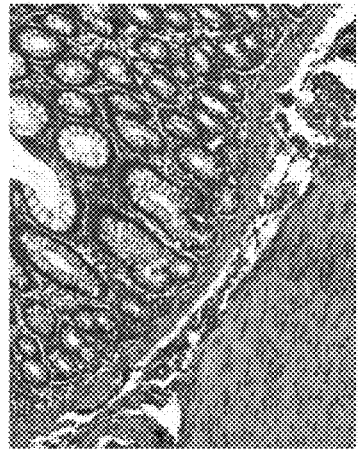
Fig. 12a
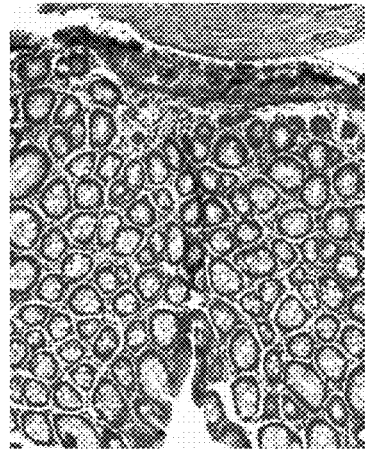
Fig. 12d
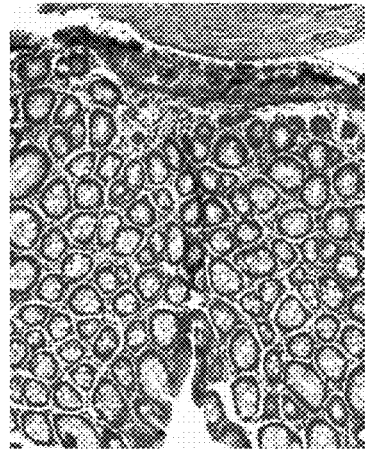
Fig. 12e
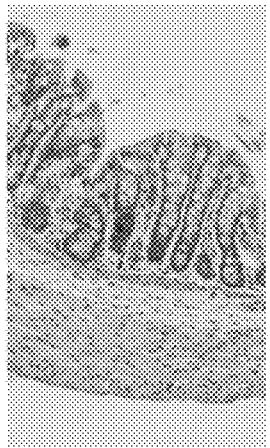
Fig. 12b
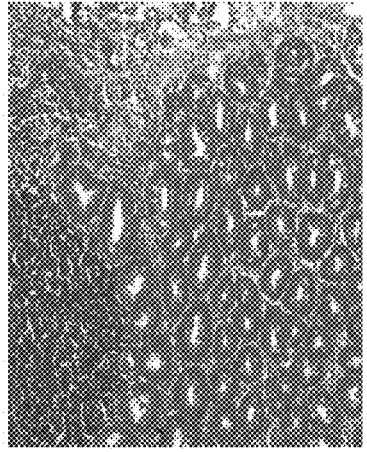
Fig. 12c

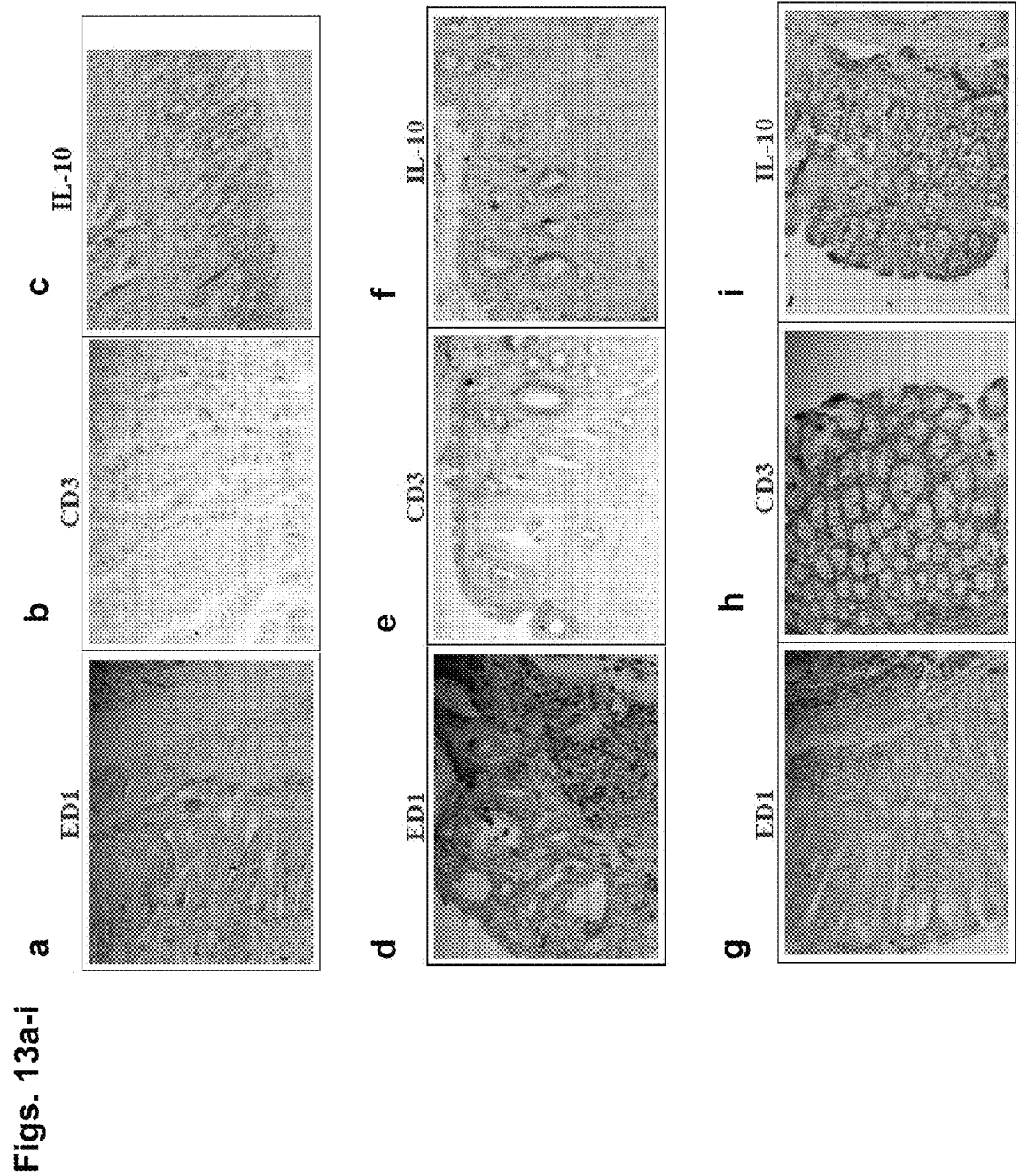
Figs. 13a-i

SEQUENCE LISTING

```
<160> NUMBER OF SEQ ID NOS: 36

<210> SEQ ID NO 1
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 1
ccatgggcgg cagctccagg gc                                              22

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
ctacagcttg gcttcttgca c                                               21

<210> SEQ ID NO 3
<211> LENGTH: 1531
<212> TYPE: DNA
<213> ORGANISM: Rattus norvegicus

<400> SEQUENCE: 3
catgggcggc agctccaggg cacgctgggt ggccttgggg ctgggcgttc tagggctgct      60
gtgtgctgcg ctcggcgtta tcgtgattct catggtgccc tcgctcatca aacagcaggt     120
gctcaagaat gtccgcatag accccagcag cctgtccttt gggatgtgga aggagatccc     180
tgttcccttc tacttgtccg tctacttctt cgaggtggtc aaccccagcg aggtcctaaa     240
tggccagaag ccagtagtcc gggagcgcgg accctatgtc tacagggagt tcagacaaaa     300
ggttaacatc accttcaatg acaatgacac ggtgtcctac atagagaacc gaagccttca     360
tttccagcca gacaggtccc agggctcaga gagtgactac attgtactgc taacatcct      420 ggtcctggga ggggcagtga tgatggagga caagcccaca agcctgaagc tgctaatgac     480
cttggggttg gtcaccatgg ccagcgggc ctttatgaac cgcacggttg gtgagatcct      540
gtggggctat gaggatccgt tcgtgaattt cctcagcaaa tatttcccag acatgttccc     600
catcaaaggc aaatttggcc tgttcgttgg gatgaaccac tcagagttct ggctcttcac     660
cgtcttacag ggtgtccaga atttcagcaa gatccatctg gtggataagt ggaacggcct     720
cagcgaggtc aaatattggc attcggaaca gtgcaacatg atcaatggta ctgccgggca     780
gatgtgggca ccattcatga cacccgaatc ctcactggaa ttcttcagcc cagaagcctg     840
cagatctatg aagctcacct accaggaatc aagggtgttc gaaggcatcc ccacttatcg     900
cttcacggcc cccgatactt tgtttgccaa cgggtccgtc tacccaccta tgaaggctt      960
```

-continued

```
ctgcccgtgc cgcgagtccg gcattcagaa tgtcagcacc tgcaggtttg gtgcgcccct    1020
gtttctctcc cagccccact tctacaatgc tgacccc gtg ctgtcagaag ctgttcttgg    1080
tctgaaccct gacccaaggg agcattcttt gttccttgac atccacccgg tcactgggat    1140
ccccatgaac tgttccgtga agatgcagct gagtctgtac atcaaatccg tcaagggcgt    1200
cgggcaaaca gggaagatcg agccagtagt cctgccattg ctgtggttcg aacagagcgg    1260
gatgatgggt ggcaagaccc tgaacacgtt ctacacgcag ctggtgctga tgccccaggt    1320
tcttcactac gcgcagtatg tgctgctggg gcttggaggc ctcctgctgc tggtgcccat    1380
catttaccaa ctgcgcagcc aggagaaatg cttttattt tggagtggta gtaaaaaggg    1440
ctcgcaggat aaggaggcca tgcaggccta ctctgagtct ctgatgtcac cagctgccaa    1500
gggcacggta gtgcaagaag ccaagctgta g                                  1531
```

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4

```
atggatgacg atatcgctgc gctc                                            24
```

<210> SEQ ID NO 5
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 5

```
ctaccggcca gccagacg                                                   18
```

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6

```
ccatgggctg ctccgccaaa                                                 20
```

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7

```
ctacagtttt gcttcctgca g                                               21
```

<210> SEQ ID NO 8
<211> LENGTH: 1530
<212> TYPE: DNA
<213> ORGANISM: Homo sapiens

<400> SEQUENCE: 8

```
atgggctgct ccgccaaagc gcgctgggct gccggggcgc tgggcgtcgc ggggctactg    60
tgcgctgtgc tgggcgctgt catgatcgtg atggtgccgt cgctcatcaa gcagcaggtc    120
```

```
cttaagaacg tgcgcatcga ccccagtagc ctgtccttca acatgtggaa ggagatccct    180 atcccttct atctctccgt ctacttcttt gacgtcatga ccccagcga atcctgaag      240 ggcgagaagc cgcaggtgcg ggagcgcggg ccctacgtgt acagggagtc caggcacaaa    300
agcaacatca ccttcaacaa caacgacacc gtgtccttcc tcgagtaccg caccttccag    360
ttccagccct ccaagtccca cggctcggag agcgactaca tcgtcatgcc caacatcctg    420
gtcttgggtg cggcggtgat gatggagaat aagcccatga ccctgaagct catcatgacc    480
ttggcattca ccaccctcgg cgaacgtgcc ttcatgaacc gcactgtggg tgagatcatg    540
tggggctaca aggacccccct tgtgaatctc atcaacaagt actttccagg catgttcccc    600
ttcaaggaca agttcggatt atttgctgag ctcaacaact ccgactctgg gctcttcacg    660
gtgttcacgg gggtccagaa catcagcagg atccacctcg tggacaagtg aacgggctg     720 agcaaggttg acttctggca ttccgatcag tgcaacatga tcaatggaac ttctgggcaa    780
atgtggccgc ccttcatgac tcctgagtcc tcgctggagt tctacagccc ggaggcctgc    840
cgatccatga agctaatgta caaggagtca ggggtgtttg aaggcatccc cacctatcgc    900
ttcgtggctc ccaaaaccct gtttgccaac gggtccatct acccacccaa cgaaggcttc    960
tgcccgtgcc tggagtctgg aattcagaac gtcagcacct gcaggttcag tgccccttg    1020 tttctctccc atcctcactt cctcaacgcc gacccggttc tggcagaagc ggtgactggc   1080
ctgcacccta accaggaggc acactccttg ttcctggaca tccacccggt cacgggaatc   1140
cccatgaact gctctgtgaa actgcagctg agcctctaca tgaaatctgt cgcaggcatt   1200
ggacaaactg ggaagattga gcctgtggtc ctgccgctgc tctggtttgc agagagcggg   1260
gccatggagg gggagactct tcacacattc tacactcagc tggtgttgat gcccaaggtg   1320
atgcactatg cccagtacgt cctcctggcg ctgggctgcg tcctgctgct ggtccctgtc   1380
atctgccaaa tccggagcca agagaaatgc tatttatttt ggagtagtag taaaagggc    1440 tcaaaggata aggaggccat tcaggcctat tctgaatccc tgatgacatc agctcccaag   1500
ggctctgtgc tgcaggaagc aaaactgtag                                   1530
```

<210> SEQ ID NO 9
<211> LENGTH: 23
<212> TYPE: PRT
<213> ORGANISM: Artificial sequence
<220> FEATURE:
<223> OTHER INFORMATION: E12 light chain, framework 1 (FWR1) amino acid
      sequence

<400> SEQUENCE: 9

Asp Ile Val Met Ser Gln Ser Pro Ala Ser Leu Ala Val Ser Leu Gly
1               5                   10                  15

Gln Arg Ala Thr Ile Ser Tyr
            20

<210> SEQ ID NO 10
<211> LENGTH: 69
<212> TYPE: DNA
<213> ORGANISM: Artificial sequence
<220> FEATURE:
<223> OTHER INFORMATION: E12 light chain, framework 1 (FWR1) encoding
      nucleic acid sequence

<400> SEQUENCE: 10

```
gacattgtga tgtcacagtc tcctgcttcc ttagctgtat ctctggggca gagggccacc    60
atctcatac                                                            69
```

```
<210> SEQ ID NO 11
<211> LENGTH: 15
<212> TYPE: PRT
<213> ORGANISM: Artificial sequence
<220> FEATURE:
<223> OTHER INFORMATION: E12 light chain, CDR1 amino acid sequence

<400> SEQUENCE: 11

Arg Ala Ser Lys Ser Val Ser Thr Ser Gly Tyr Ser Tyr Met His
1               5                  10                  15

<210> SEQ ID NO 12
<211> LENGTH: 45
<212> TYPE: DNA
<213> ORGANISM: Artificial sequence
<220> FEATURE:
<223> OTHER INFORMATION: E12 light chain, CDR1 encoding nucleic acid
      sequence

<400> SEQUENCE: 12
agggccagca aaagtgtcag tacatctggc tatagttata tgcac            45

<210> SEQ ID NO 13
<211> LENGTH: 15
<212> TYPE: PRT
<213> ORGANISM: Artificial sequence
<220> FEATURE:
<223> OTHER INFORMATION: E12 light chain, framework 2 (FWR2) amino acid
      sequence

<400> SEQUENCE: 13

Trp Asn Gln Gln Lys Pro Gly Gln Pro Pro Arg Pro Leu Ile Tyr
1               5                  10                  15

<210> SEQ ID NO 14
<211> LENGTH: 45
<212> TYPE: DNA
<213> ORGANISM: Artificial sequence
<220> FEATURE:
<223> OTHER INFORMATION: E12 light chain, framework 2 (FWR2) encoding
      nucleic acid sequence

<400> SEQUENCE: 14
tggaaccaac agaaaccagg acagccaccc agacccctca tctat            45

<210> SEQ ID NO 15
<211> LENGTH: 7
<212> TYPE: PRT
<213> ORGANISM: Artificial sequence
<220> FEATURE:
<223> OTHER INFORMATION: E12 light chain, CDR2 amino acid sequence

<400> SEQUENCE: 15

Leu Val Ser Asn Leu Glu Ser
1               5

<210> SEQ ID NO 16
<211> LENGTH: 21
<212> TYPE: DNA
<213> ORGANISM: Artificial sequence
<220> FEATURE:
<223> OTHER INFORMATION: E12 light chain, CDR2  encoding nucleic acid
      sequence

<400> SEQUENCE: 16
cttgtatcca acctagaatc t                                      21
```

```
<210> SEQ ID NO 17
<211> LENGTH: 32
<212> TYPE: PRT
<213> ORGANISM: Artificial sequence
<220> FEATURE:
<223> OTHER INFORMATION: E12 light chain, framework 3 (FWR3) amino acid
      sequence

<400> SEQUENCE: 17

Gly Val Pro Ala Arg Phe Ser Gly Ser Gly Ser Gly Thr Asp Phe Thr
1               5                   10                  15

Leu Asn Ile His Pro Val Glu Gly Glu Asp Ala Ala Thr Tyr Tyr Cys
            20                  25                  30

<210> SEQ ID NO 18
<211> LENGTH: 96
<212> TYPE: DNA
<213> ORGANISM: Artificial sequence
<220> FEATURE:
<223> OTHER INFORMATION: E12 light chain, framework 3 (FWR3) encoding
      nucleic acid sequence

<400> SEQUENCE: 18
ggggtccctg ccaggttcag tggcagtggg tctgggacag acttcaccct caacatccat      60
cctgtggagg gggaggatgc tgcaacctat tactgt                                96

<210> SEQ ID NO 19
<211> LENGTH: 9
<212> TYPE: PRT
<213> ORGANISM: Artificial sequence
<220> FEATURE:
<223> OTHER INFORMATION: E12 light chain, CDR3 amino acid sequence

<400> SEQUENCE: 19

Gln His Ile Arg Glu Leu Thr Arg Ser
1               5

<210> SEQ ID NO 20
<211> LENGTH: 27
<212> TYPE: DNA
<213> ORGANISM: Artificial sequence
<220> FEATURE:
<223> OTHER INFORMATION: E12 light chain, CDR3 encoding nucleic acid
      sequence

<400> SEQUENCE: 20
cagcacatta gggagcttac acgttcg                                          27

<210> SEQ ID NO 21
<211> LENGTH: 27
<212> TYPE: PRT
<213> ORGANISM: Artificial sequence
<220> FEATURE:
<223> OTHER INFORMATION: E12 light chain, framework 4 (FWR4) amino acid
      sequence

<400> SEQUENCE: 21

Glu Gly Ala Gln Asn Trp Lys Ser Asn Gly Arg Pro Gln Val Ala Ile
1               5                   10                  15

Gly Ser Arg Ala Arg Arg Leu Gln Arg Pro Ala
            20                  25

<210> SEQ ID NO 22
<211> LENGTH: 81
<212> TYPE: DNA
<213> ORGANISM: Artificial sequence
<220> FEATURE:
```

<223> OTHER INFORMATION: E12 light chain, framework 4 (FWR4) encoding
nucleic acid sequence

<400> SEQUENCE: 22 gaggggggcac aaaactggaa atcaaacggg cggccgcagg tggcaatcgg atcccgggcc    60
cgtcgactgc agaggcctgc a                                              81

<210> SEQ ID NO 23
<211> LENGTH: 29
<212> TYPE: PRT
<213> ORGANISM: Artificial sequence
<220> FEATURE:
<223> OTHER INFORMATION: E12 heavy chain, framework 1 (FWR1) amino acid
sequence

<400> SEQUENCE: 23

Val Lys Leu Val Glu Ser Gly Gly Gly Leu Val Gln Pro Gly Gly Ser
1               5                   10                  15

Leu Arg Leu Ser Cys Ala Thr Ser Gly Phe Thr Phe Thr
            20                  25

<210> SEQ ID NO 24
<211> LENGTH: 87
<212> TYPE: DNA
<213> ORGANISM: Artificial sequence
<220> FEATURE:
<223> OTHER INFORMATION: E12 heavy chain, framework 1 (FWR1) encoding
nucleic acid sequence

<400> SEQUENCE: 24
gtgaagctgg tggaatctgg aggaggcttg gtacagcctg ggggttctct gagactctcc    60
tgtgcaactt ctgggttcac cttcact                                        87

<210> SEQ ID NO 25
<211> LENGTH: 5
<212> TYPE: PRT
<213> ORGANISM: Artificial sequence
<220> FEATURE:
<223> OTHER INFORMATION: E12 heavy chain, CDR1 amino acid sequence

<400> SEQUENCE: 25

Asp Tyr Tyr Met Ser
1               5

<210> SEQ ID NO 26
<211> LENGTH: 15
<212> TYPE: DNA
<213> ORGANISM: Artificial sequence
<220> FEATURE:
<223> OTHER INFORMATION: E12 heavy chain, CDR1 encoding nucleic acid
sequence

<400> SEQUENCE: 26
gattactaca tgagc                                                     15

<210> SEQ ID NO 27
<211> LENGTH: 14
<212> TYPE: PRT
<213> ORGANISM: Artificial sequence
<220> FEATURE:
<223> OTHER INFORMATION: E12 heavy chain, framework 2 (FWR2) amino acid
sequence

<400> SEQUENCE: 27

Trp Val Arg Gln Pro Pro Gly Lys Ala Leu Glu Trp Leu Gly
1               5                   10

<210> SEQ ID NO 28
<211> LENGTH: 42
<212> TYPE: DNA
<213> ORGANISM: Artificial sequence
<220> FEATURE:
<223> OTHER INFORMATION: E12 heavy chain, framework 2 (FWR2) encoding
      nucleic acid sequence

<400> SEQUENCE: 28
tgggtccgcc agcctccagg aaaggcactt gagtggttgg gt                          42

<210> SEQ ID NO 29
<211> LENGTH: 19
<212> TYPE: PRT
<213> ORGANISM: Artificial sequence
<220> FEATURE:
<223> OTHER INFORMATION: E12 heavy chain, CDR2 amino acid sequence

<400> SEQUENCE: 29

Phe Ile Arg Asn Lys Gly Asn Gly Tyr Thr Thr Glu Tyr Ser Ala Ser
1               5                   10                  15

Val Lys Gly

<210> SEQ ID NO 30
<211> LENGTH: 57
<212> TYPE: DNA
<213> ORGANISM: Artificial sequence
<220> FEATURE:
<223> OTHER INFORMATION: E12 heavy chain, CDR2  encoding nucleic acid
      sequence

<400> SEQUENCE: 30
tttattagaa acaaaggtaa tggttacaca acagagtaca gtgcatctgt gaagggt          57

<210> SEQ ID NO 31
<211> LENGTH: 32
<212> TYPE: PRT
<213> ORGANISM: Artificial sequence
<220> FEATURE:
<223> OTHER INFORMATION: E12 heavy chain, framework 3 (FWR3) amino acid
      sequence

<400> SEQUENCE: 31

Arg Phe Thr Ile Ser Arg Asp Asn Ser Gln Ser Ile Leu Tyr Leu Gln
1               5                   10                  15

Met Asn Thr Leu Arg Ala Glu Asp Ser Ala Thr Tyr Tyr Cys Ala Arg
                20                  25                  30

<210> SEQ ID NO 32
<211> LENGTH: 96
<212> TYPE: DNA
<213> ORGANISM: Artificial sequence
<220> FEATURE:
<223> OTHER INFORMATION: E12 heavy chain, framework 3 (FWR3) encoding
      nucleic acid sequence

<400> SEQUENCE: 32
cggttcacca tctccagaga taattcccaa agcatcctct atcttcaaat gaacaccctg       60
agagctgagg acagtgccac ttattactgt gcaaga                                 96

<210> SEQ ID NO 33
<211> LENGTH: 14
<212> TYPE: PRT
<213> ORGANISM: Artificial sequence
<220> FEATURE:

```
<223> OTHER INFORMATION: E12 heavy chain, CDR3 amino acid sequence

<400> SEQUENCE: 33

Asp Gly Tyr Tyr Gly Asn Tyr Val Gly Tyr Ala Met Asp Tyr
1               5                   10

<210> SEQ ID NO 34
<211> LENGTH: 42
<212> TYPE: DNA
<213> ORGANISM: Artificial sequence
<220> FEATURE:
<223> OTHER INFORMATION: E12 heavy chain, CDR3 encoding nucleic acid
      sequence

<400> SEQUENCE: 34
gatggatact atggtaacta cgtgggctat gctatggact ac                          42

<210> SEQ ID NO 35
<211> LENGTH: 11
<212> TYPE: PRT
<213> ORGANISM: Artificial sequence
<220> FEATURE:
<223> OTHER INFORMATION: E12 heavy chain, framework 4 (FWR4) amino acid
      sequence

<400> SEQUENCE: 35

Trp Gly Gln Gly Thr Ser Val Thr Val Ser Ser
1               5                   10

<210> SEQ ID NO 36
<211> LENGTH: 33
<212> TYPE: DNA
<213> ORGANISM: Artificial sequence
<220> FEATURE:
<223> OTHER INFORMATION: E12 heavy chain, framework 4 (FWR4) encoding
      nucleic acid sequence

<400> SEQUENCE: 36
tggggtcaag gaacctcagt caccgtctcc tcg                                    33
```

COMPOSITIONS AND METHODS FOR DIAGNOSING AND TREATING AN INFLAMMATION

RELATED APPLICATION/S

This application is a continuation of U.S. patent application Ser. No. 11/222,745 filed on Sep. 12, 2005, now U.S. Pat. No. 8,017,113, which is a Continuation-In-Part (CIP) of PCT Application No. PCT/IL2004/000241 filed on Mar. 14, 2004, which claims the benefit of priority from U.S. Provisional Patent Application Nos. 60/453,512 and 60/453,514 both filed on Mar. 12, 2003. The contents of the above applications are incorporated herein by reference.

FIELD AND BACKGROUND OF THE INVENTION

The present invention relates to antibodies, compositions and methods for diagnosing and treating inflammation. More particularly, the present invention relates to the use of scavenger receptor inhibitors in treatment of an inflammatory response and to methods of diagnosing an inflammatory response via detection of autoantibodies directed at scavenger receptors.

Inflammation is a physiological condition characterized in the acute form by the classical signs of pain, heat, redness, swelling and loss of function. Inflammation often accompanies diseases such as Multiple Sclerosis (MS), osteoarthritis, Inflammatory Bowl Disease (IBD) including Crohn's disease and ulcerative colitis, Rheumatoid Arthritis (RA), SLE, type I diabetes (IDDM), atherosclerosis, encephalomyelitis, Alzheimer's disease, stroke, traumatic brain injury, Parkinson's disease, septic shock and others. In most cases, there is no effective cure for inflammation associated with such disease and existing treatments are palliative and largely fail to control the underlying causes of tissue degradation.

Scavenger receptors (SRs) are cell surface proteins, which are typically found on macrophages and bind various types of chemically modified lipoproteins (1-3), such as low-density lipoprotein (LDL). This family of trans-membrane receptors which are highly varied in structure are involved in receptor-mediated endocytosis, phagocytosis of apoptotic cells and bacteria, as well as in cell adhesion [Peiser L. et al., Curr. Opin. Immun. 14(1):123-128, 2002]. Since the massive receptor-mediated uptake of cholesterol from modified LDL can convert cultured macrophages into cholesteryl ester-filled foam cells, similar to those found in atherosclerotic plaques, it has been postulated that these receptors also function in deposition of LDL cholesterol of macrophages in artery walls during the initial stages of atherosclerotic plaque formation [1].

Scavenger receptors (SRs) are termed as such since they mediate the binding of remarkably wide variety of polyanionic ligands [e.g., modified proteins, sulfated polysaccharides and certain polynucleotides [1, 3, 4]. This property led to the hypothesis that these receptors form a part of an in innate immune response by serving as pattern recognition receptors that bind a wide variety of pathogen components [2-5].

SR-B1 (also referred to as SR-BI or CLA-I) is a macrophage scavenger molecule and a receptor for high-density lipoprotein (HDL) [2, 3, 6, 7] that mediates cholesterol uptake from cells [Rigotti A. et al., Curr. Opin. Lipidol., 8:181-8, 1997; Rigotti A. et al., Proc. Natl. Acad. Sci., 94:12610-5, 1997]. SR-B1 can also serve as a receptor for non-HDL lipoproteins and appears to play an important role in reverse cholesterol transport. In vivo experiments showed that this receptor is important for HDL metabolism in mice, and for the metabolism of LDL and HDL cholesterol in humans [Stang H. et al., J. Biol. Chem. 274:32692-8., 1999; Swarnakar S. et al., J. Biol. Chem. 274:29733-9., 1999]. Studies involving the manipulation of SR-B1 gene expression in mice, indicate that its expression protects against atherosclerosis [Kozarsky K. F., and Krieger M., Curr. Opin. Lipidol. 10:491-7., 1999; Ueda Y. et al., J. Biol. Chem. 275:20368-73., 2000; Acton S. L. et al., Mol. Med. Today 5:518-24., 1999]. It was also suggested that HDL and particularly its protein fraction Apo-A1 affect the in vitro production of pro-inflammatory mediators by macrophages (8). Among mediators derived from macrophages that propagate inflammation are interleukin 12 (IL-12), TNF-α and possibly IL-6 whereas, TGF-β and IL-10 have predominantly anti-inflammatory effects [Kiefer R. et al., Prog. Neurobiol. 64(2):109-27, 2001].

PCT Publication No. WO 2004/041179 teaches targeting of scavenger receptor SR-B1 (Cla-I) for the treatment of infection, sepsis and inflammation. This prior art teaches primarily targeting SR-B1 using amphipathic peptides which compete the amphipathic helices in apoliprotein ligands of SR-B1. PCT Publication No. WO 2004/041179 does not provide experimental results for treating autoimmune diseases such as IBD and multiple sclerosis by down-regulating activity or expression of SR-B1, nor does it teach the use of oligonucleotide technology (e.g., antisense, siRNA) and DNA vaccination for targeting SR-B1 and treating inflammatory diseases.

There is thus, a widely recognized need for and it would be highly advantageous to have novel agents and methods using same for targeting SR-B1 and treating inflammatory diseases.

SUMMARY OF THE INVENTION

According to one aspect of the present invention there is provided a method of reducing an inflammatory response in a subject, the method comprising providing to a subject in need thereof a therapeutically effective amount of an agent capable of reducing activity and/or expression of a scavenger receptor or of an effector thereof, thereby reducing the inflammatory response in the subject.

According to further features in preferred embodiments of the invention described below, the agent is selected from the group consisting of: (i) an oligonucleotide directed to an endogenous nucleic acid sequence expressing the scavenger receptor or the effector thereof; (ii) a chemical inhibitor directed to the scavenger receptor or the effector thereof; (iii) a neutralizing antibody directed at the scavenger receptor or the effector thereof; (iv) a non-functional derivative of the scavenger receptor or the effector thereof; and (v) a DNA vaccine to scavenger receptor or the effector thereof.

According to still further features in the described preferred embodiments the scavenger receptor is a class A scavenger receptor or a class B scavenger receptor.

According to still further features in the described preferred embodiments the class B scavenger receptor is SR-BI.

According to another aspect of the present invention there is provided use of an agent capable of reducing activity and/or expression of scavenger receptor or of an effector thereof for the manufacture of a medicament for the treatment of inflammatory diseases.

According to yet another aspect of the present invention there is provided an article of manufacture comprising packaging material and a pharmaceutical composition identified for treating inflammatory diseases being contained within the packaging material, the pharmaceutical composition including, as an active ingredient, an agent capable of reducing activity and/or expression of scavenger receptor or of an effector thereof and a pharmaceutically acceptable carrier.

According to still another aspect of the present invention there is provided a method of diagnosing predisposition to, or presence of, an inflammatory disease in a subject, the method comprising detecting anti scavenger receptor antibodies in a biological sample obtained from the subject, wherein a level above a predetermined normal threshold of the anti scavenger receptor antibodies in the biological sample is indicative of the inflammatory disease in the subject.

According to still further features in the described preferred embodiments detecting the anti scavenger receptor antibodies in the biological sample is effected by ELISA, RIA and/or dot blot.

According to an additional aspect of the present invention there is provided a humanized antibody having an antigen recognition domain capable of specifically binding a scavenger receptor.

According to yet an additional aspect of the present invention there is provided an isolated polypeptide comprising an antigen recognition domain capable of specifically binding a human scavenger receptor and neutralize an activity thereof.

According to still further features in the described preferred embodiments the polypeptide is an antibody or an antibody fragment.

According to still further features in the described preferred embodiments the antibody or antibody fragment is humanized.

According to still further features in the described preferred embodiments the antibody or the antibody fragment is selected from the group consisting of a Fab fragment, an Fv fragment, a single chain antibody and a single domain antibody.

According to still further features in the described preferred embodiments the polypeptide is a CDR-containing recombinant polypeptide.

According to still further features in the described preferred embodiments an amino acid sequence of the CDR is selected from the group consisting of SEQ ID NO: 11, 15, 19, 25, 29 and 33.

According to still an additional aspect of the present invention there is provided an isolated polynucleotide comprising a nucleic acid sequence encoding the recombinant polypeptide.

According to still further features in the described preferred embodiments the antigen recognition domain is capable of specifically recognizing a surface exposed epitope of Scavenger Receptor.

According to a further aspect of the present invention there is provided a pharmaceutical composition comprising as an active ingredient the polypeptide comprising an antigen recognition domain capable of specifically binding a human scavenger receptor and neutralize an activity thereof.

According to a further aspect of the present invention there is provided a method of reducing an inflammatory response in a subject, the method comprising providing to a subject in need thereof a therapeutically effective amount of the polypeptide comprising an antigen recognition domain capable of specifically binding a human scavenger receptor and neutralize an activity thereof, thereby reducing the inflammatory response in the subject.

According to yet a further aspect of the present invention there is provided a method of treating IBD in a subject, the method comprising providing to a subject in need thereof a therapeutically effective amount of an agent capable of reducing activity and/or expression of a scavenger receptor or of an effector thereof, thereby treating the IBD in the subject.

According to still a further aspect of the present invention there is provided a method of treating multiple sclerosis in a subject, the method comprising providing to a subject in need thereof a therapeutically effective amount of an agent capable of reducing activity and/or expression of a scavenger receptor or of an effector thereof, thereby treating multiple sclerosis in the subject.

According to still a further aspect of the present invention there is provided a method of treating IBD in a subject, the method comprising providing to a subject in need thereof a therapeutically effective amount of the polypeptide comprising an antigen recognition domain capable of specifically binding a human scavenger receptor and neutralize an activity thereof, thereby treating the IBD in the subject.

According to still a further aspect of the present invention there is provided a method of treating multiple sclerosis in a subject, the method comprising providing to a subject in need thereof a therapeutically effective amount of the polypeptide comprising an antigen recognition domain capable of specifically binding a human scavenger receptor and neutralize an activity thereof, thereby treating the multiple sclerosis in the subject.

According to still a further aspect of the present invention there is provided use of the polypeptide comprising an antigen recognition domain capable of specifically binding a human scavenger receptor and neutralize an activity thereof for the manufacture of a medicament identified for treating IBD.

According to still a further aspect of the present invention there is provided use of the polypeptide comprising an antigen recognition domain capable of specifically binding a human scavenger receptor and neutralize an activity thereof for the manufacture of a medicament identified for treating multiple sclerosis.

According to still a further aspect of the present invention there is provided a CDR-containing polypeptide having a CDR sequence selected from the group consisting of SEQ ID NO: 11, 15, 19, 25, 29 and 33.

According to still a further aspect of the present invention there is provided an isolated polynucleotide encoding the CDR-containing polypeptide having a CDR sequence selected from the group consisting of SEQ ID NO: 11, 15, 19, 25, 29 and 33.

According to still further features in the described preferred embodiments the isolated polynucleotide comprises a nucleic acid sequence selected from the group consisting of SEQ ID NO: 12, 16, 20, 26, 30 and 32.

The present invention successfully addresses the shortcomings of the presently known configurations by providing novel compositions and methods containing same for diagnosing and treating an inflammatory response.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 3:
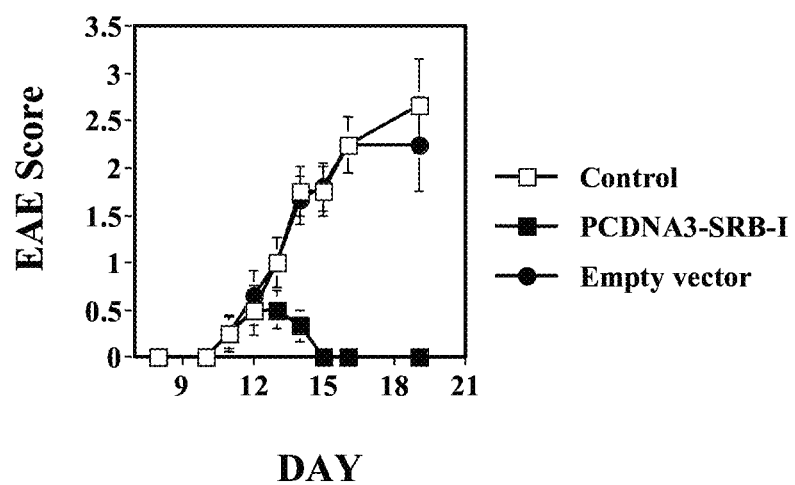
Figure 4:
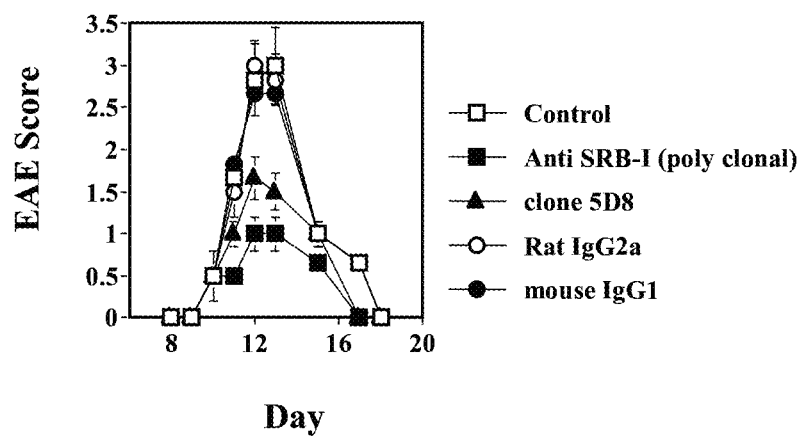
Figure 5A:
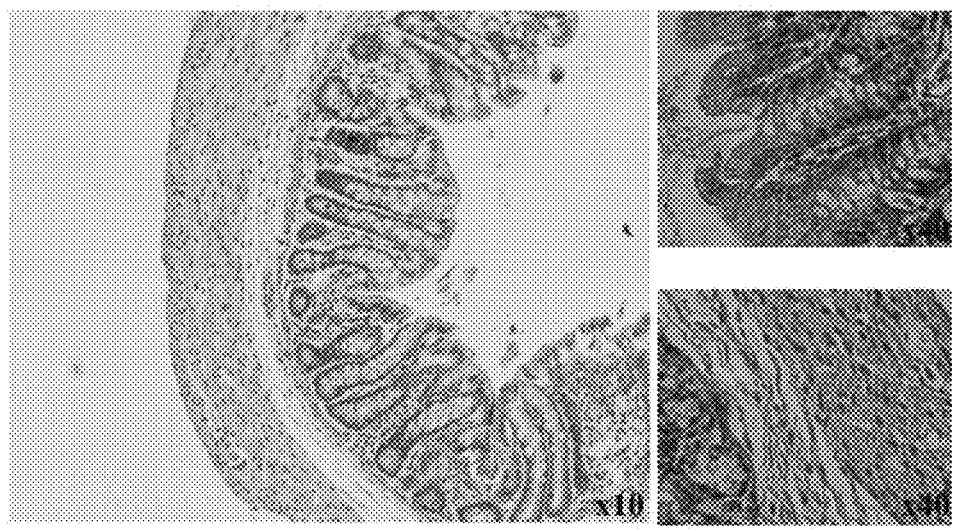
Figure 5B:
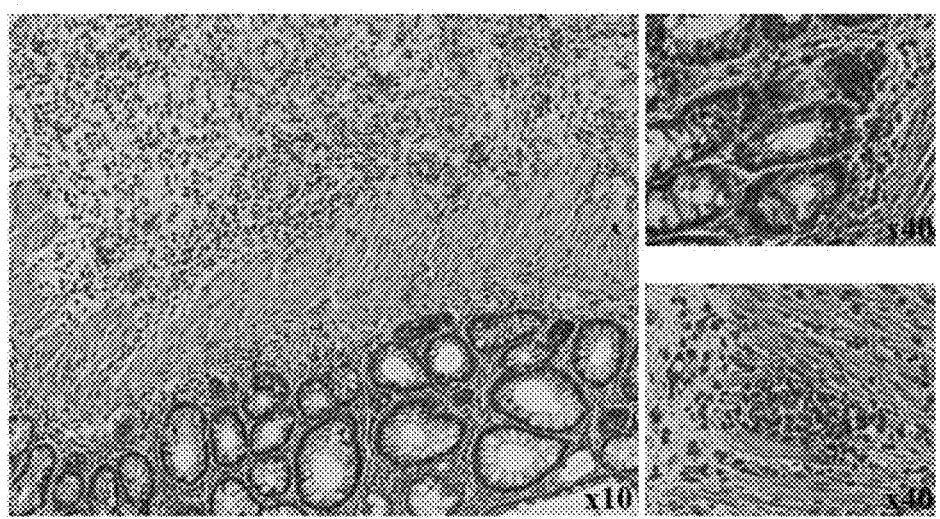
Figure 5C:
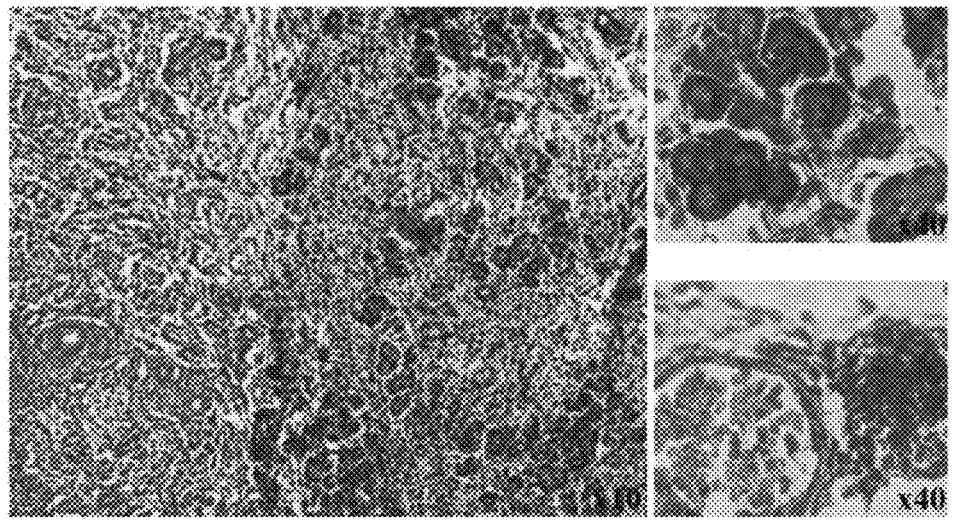
Figure 5D:
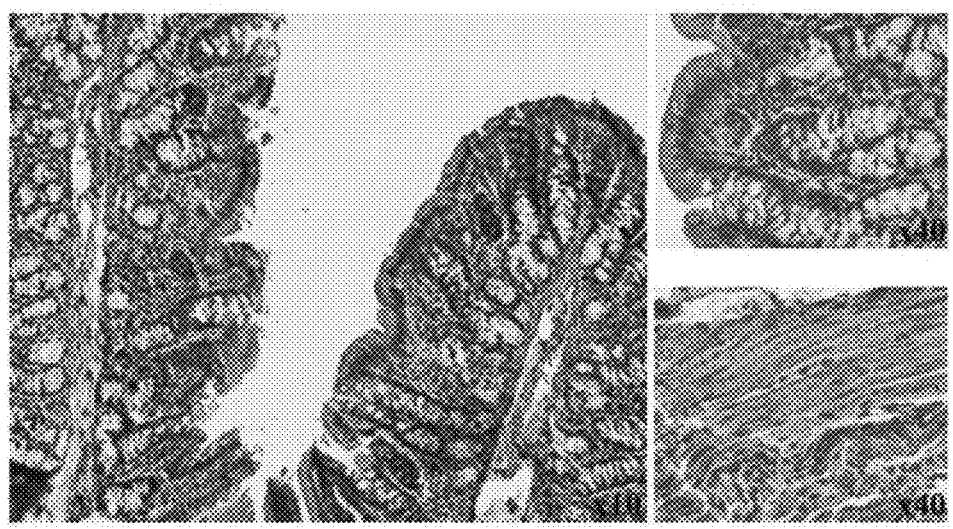
Figure 6:
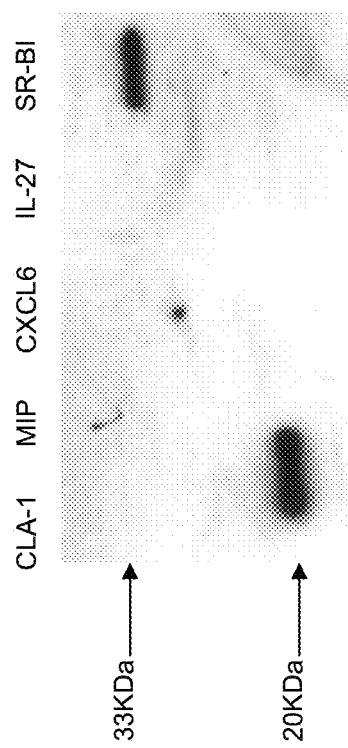
Figure 7:
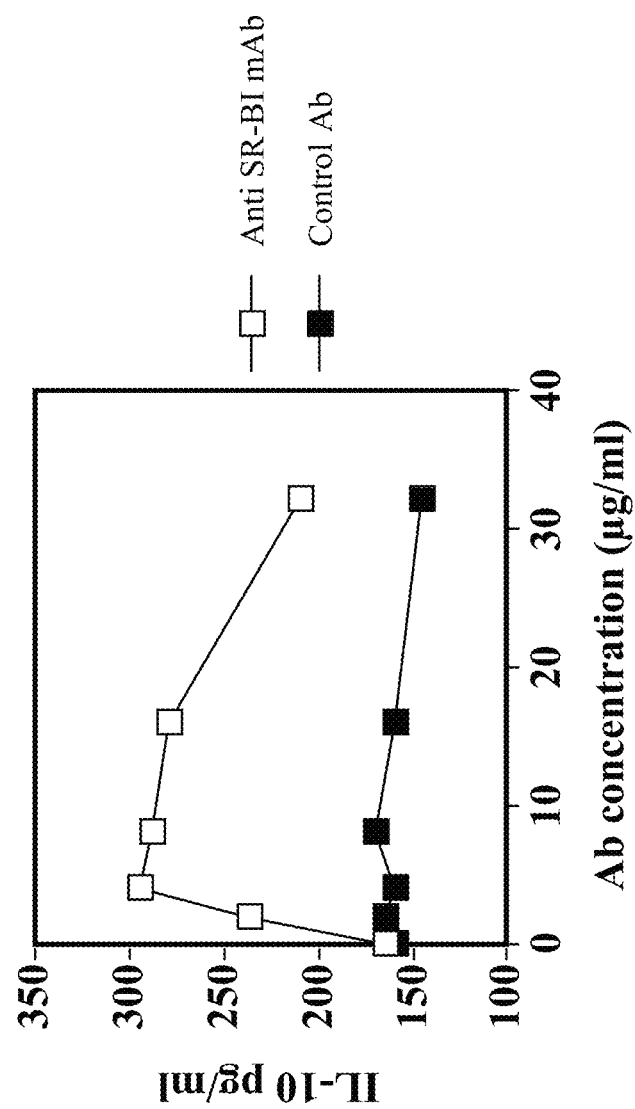
Figure 8:
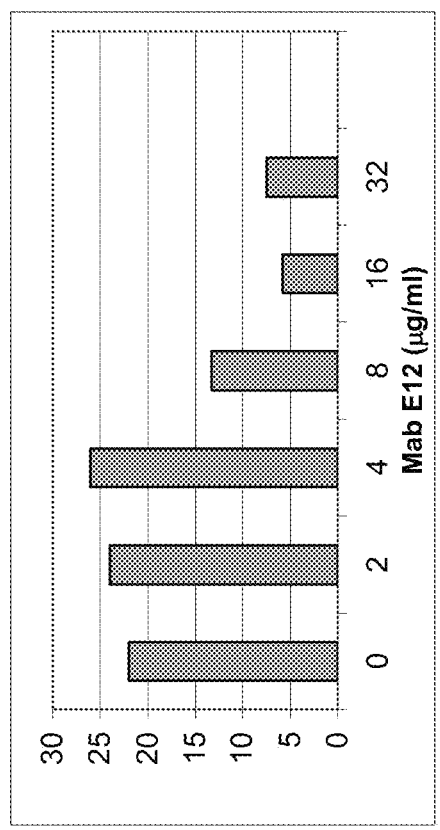
Figure 9:
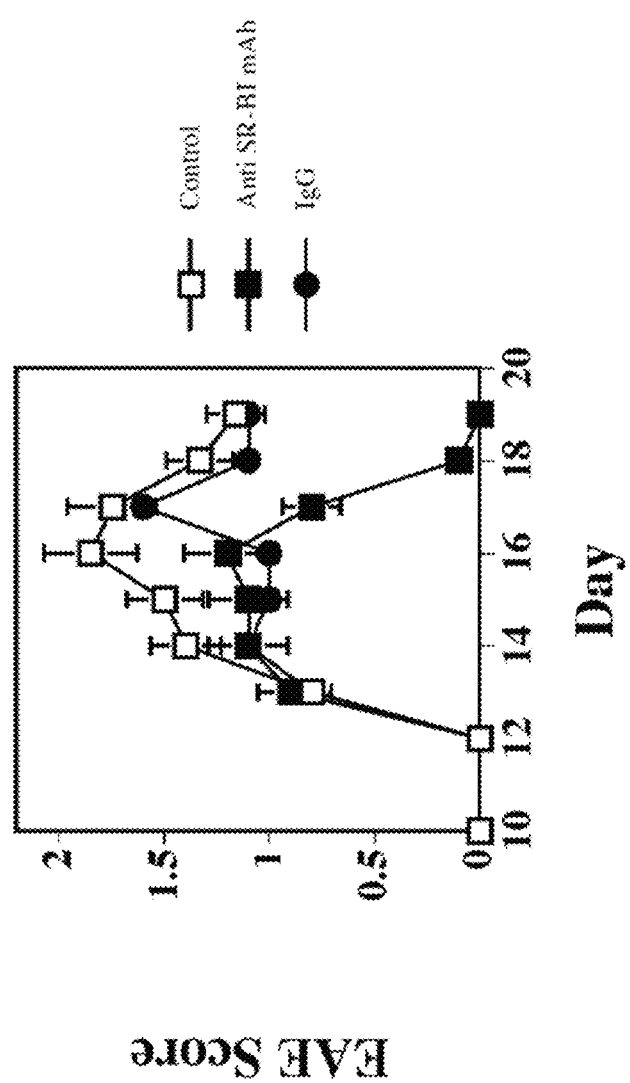

FIGS. 1a-d are graphs depicting the therapeutic effect of recombinant SR-B1 injection on EAE-induced Lewis rats. FIG. 1a is a plot graph depicting the daily development of clinical manifestations of EAE in Lewis rats previously subjected to SR-B1 vaccination. The plots compare rats (6 Lewis rats in each group) subjected to active induction of EAE, two months following last administration of plasmid DNA encoding SR-B1 (opened triangles), plasmid DNA encoding β-actin (opened squares), or PBS (closed squares). Data was obtained by an observer blind to the experimental protocol using discrete scoring (0-4) of EAE clinical manifestations as described in Example 1 of the Examples section. Results are presented as mean maximal score±SE. FIG. 1b is a bar graph depicting antibody titer in Lewis rats sera in response to administration of recombinant SR-B1. Lewis rats were subjected to repeated administration of plasmid DNA encoding SR-B1, plasmid DNA encoding β-actin, or PBS (none). Two months after the last immunization all rats were subjected to active induction of EAE and sera was taken after 13 days and determined for the development of antibody titer to recombinant SR-B1. Data was obtained by ELISA, in which rat antisera, detected the recombinant SR-B1 (OR soluble β-ACTIN) coated onto 96 well ELISA plates. Antibodies were labeled with Goat anti-rat IgG alkaline phosphatase conjugated antibody and in the presence of p-Nitrophenyl Phosphate (p-NPP) liquid substrate produces absorbance at 405 nm. Data was collected using ELISA reader. Results are presented as $\log_2$-Ab titer±SE. FIG. 1c is a plot graph depicting specific binding of anti SR-B1 antibodies to the native form of SR-B1 on activated peritoneal macrophages. The graphs represent flow cytometry analysis of rat activated peritoneal macrophages cells ($10^6$) incubated for 30 minutes with IgG (0.5 μg/ml) labeled with anti-rat IgG-FITC, purified from rats that were subjected to plasmid DNA encoding SR-B1 (Anti SR-BI) or to plasmid DNA encoding β-actin (control IgG) administration. Data was collected using a FACScalibur. Results are presented as relative cell number. FIG. 1d is a plot graph depicting the daily development of clinical manifestations of EAE in Lewis rats subjected to IgG administration. The plots compare rats (6 Lewis rats in each group) subjected to active induction of EAE and then repeated (days 5, 7, 9) administration of 100 μg/rat of purified IgG from EAE rats treated with plasmid DNA encoding SR-B1 (opened triangles), plasmid DNA encoding β-actin (opened squares), or PBS (closed squares). Data was obtained by an observer blind to the experimental protocol using discrete scoring (0-4) of EAE clinical manifestations as described in Example 1 of the Examples section. Results are presented as mean maximal score±SE;

FIGS. 2a-c are graphs depicting the effect of anti SR-B1 antibodies on cytokine expression by murine peritoneal macrophages. The plots compare levels of IL-12 (FIG. 2a), TNF-α (FIG. 2b) and IL-10 (FIG. 2c) produced by LPS activated murine peritoneal macrophages supplemented with (0, 10, 50 or 100 μg/ml) purified anti SR-B1 polyclonal autoantibodies (closed squares), or control IgG (open squares) from normal rat serum after 48 h incubation. Data was obtained by ELISA using commercial kits. Data was collected using ELISA reader. Results are presented in pg/ml as mean triplicates±SE;

FIG. 3 is a graph depicting the daily development of clinical manifestations of EAE in C57BL/6 mice treated with SR-B1 DNA vaccine. The plots compare treatment of mice (6 in each group) with SR-B1 encoding DNA vaccine (closed squares), empty plasmid (closed circles), or PBS (opened squares) 12 days after the onset of disease. Data was obtained by an observer blind to the experimental protocol using discrete scoring (0-4) of EAE clinical manifestations as described in Example 1 of the Examples section. Results are presented as mean maximal score±SE;

FIG. 4 is a graph depicting the daily development of clinical manifestations of EAE in Lewis rats treated with anti SR-B1 antibodies. The plots compare treatment of rats (6 Lewis rats in each group) with 100 μg/ml of monoclonal antibody 5D8 (closed triangle), control murine IgG1 (closed circles), anti SR-B1 polyclonal antibody (closed squares), control rat IgG2a purified from EAE rats that have been subjected to an empty plasmid DNA vaccination (open circles) or PBS treated control (open squares). Data was obtained by an observer blind to the experimental protocol using discrete scoring (0-4) of EAE clinical manifestations as described in Example 1 of the Examples section. Results are presented as mean maximal score±SE;

FIGS. 5a-d are photomicrographs depicting colon histology sections of colitis induced rats. FIG. 5a is a representative histology section of colon of an untreated rat (normal colon). FIG. 5b is a representative histology section of a rat colon, 15 days post induction of colitis, subjected to repeated administration of PBS (days 6, 8 and 10 post induction of the disease—control sick rat colon). FIG. 5c is a representative histology section of a rat colon, 15 days post induction of colitis, subjected to repeated administration of control IgG (days 6, 8 and 10 post induction of the disease—control IgG treated colon). FIG. 5d is a representative histology section of a rat colon, 15 days post induction of colitis, subjected to repeated administration of anti SR-B1 polyclonal antibodies (days 6, 8 and 10 post induction of the disease—anti SR-B1 treated colon). Photos were obtained using a digital camera (Nikon digital camera DXM1200F) and a light microscopy (Nikon TE2000-S);

FIG. 6 is a photograph depicting cross-reactivity of monoclonal anti SR-B1 antibody, E12, with human and mouse orthologs. Recombinant proteins were resolved on SDS-PAGE and transferred to nitrocellulose membrane. The membrane was subjected to E12;

FIG. 7 is a graph depicting dose-dependent induction of IL-10 secretion from cultured peritoneal macrophages treated with E12;

FIG. 8 is a bar graph depicting dose-dependent suppression of NO levels in cultured peritoneal macrophages treated with E12;

FIG. 9 is a graph depicting the effect of E12 (closed squares), control isotype matching antibody (circles) or no treatment on ongoing EAE in mice induced with such, as determined by reduction in EAE score;

FIGS. 10a-c are bar graphs depicting the effect of E12 (pink) or control antibodies (grey) on cytokine secretion from spleen cells of 19 day EAE-induced mice. FIG. 10a-IL-4. FIG. 10b-IL-12. FIG. 10c-L-10;

FIGS. 11a-f are photographs showing IL-10 immunostaining of Lumbar spinal cord sections from EAE induced mice (19 days of disease onset) subjected to no treatment (FIG. 11a), or treated with E12 (FIG. 11b), or isotype matching control antibody (FIG. 11c). FIGS. 11a-c shows staining with biotinylated E12 for presence of scavenger receptor expressing cells. FIGS. 11d-f shows staining with anti IL-10 antibody. Anti-SR-BI therapy reduces the histological score of EAE;

FIGS. 12a-e are photographs showing representative histological colon sections obtained at day 12 of disease onset from naïve rats (FIG. 12a), positive control rats suffering form TNBS induced IBD (FIG. 12b), rats suffering from TNBS induced IBD that were subjected to repeated administration of isotype matched control IgG (FIG. 12c) in comparison to those treated with mAb E12 (FIGS. 12d-e); and FIGS. 13a-i show representative immuno-histological sections obtained at day 12 of disease onset from control rats suffering from TNBS induced IBD (FIGS. 13a-c), rats suffering form TNBS induced IBD that were subjected to repeated administration of isotype matched control IgG (FIGS. 13d-f) in comparison to diseased rats treated with mAb E12 (FIGS. 13g-i). FIGS. 13a, d and g are stained with mAb ED1 (macrophages bio-marker); FIGS. 13b, e and h are stained with anti CD3 (T cell bio-marker) and FIGS. 13 c, f and I are stained with an anti IL-10 mAb.

DESCRIPTION OF THE PREFERRED EMBODIMENTS

The present invention is of compositions and methods which can be used for the diagnosis and treatment of inflammation. Specifically, the present invention relates to the use of scavenger receptor inhibitors in treating inflammatory response and to methods of diagnosing inflammatory response via detection of autoantibodies to scavenger receptors in subjects.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases and disorders which have significant inflammatory components are ubiquitous. Skin disorders, bowel disorders, certain degenerative neurological disorders, arthritis, autoimmune diseases and other illnesses afflict many patients. The factors underlying these disorders are varied and include infectious agents, autoimmune factors, dietary or environmental factors and genetic factors. In the majority of cases, the causative elements have not been defined and many of the key pathophysiological components have not been elucidated. Accordingly, treatment options for the majority of these diseases is suboptimal.

The present inventor has previously shown that the immune system can selectively generate autoimmunity to chemokines and other proinflammatory mediators when such a response is beneficial for the host [9, 10, 11, 12, 14, 15]. For example, patients suffering from rheumatoid arthritis (RA) but not osteoarthritis (OA) have significant levels of autoantibodies directed to TNF-α, and therapies that neutralize the function of TNF-α suppress RA but not OA. Studies conducted by the present inventor have shown that selective amplification of these beneficial antibodies by targeted DNA vaccines provided protective immunity in experimental models (9, 10, 11, 12, 14, 15).

While reducing the present invention to practice, the present inventor uncovered that subjects suffering from inflammatory disease exhibit elevated levels of autoantibodies to scavenger receptor (SR) and showed that inhibiting SR function can prevent such diseases by altering the cytokine profile produced by macrophages from pro-inflammatory cytokines to anti-inflammatory cytokines.

As is illustrated hereinbelow and in the Examples section which follows, the present inventors were able to show that anti SR-BI (CLA-I) therapy (e.g., DNA vaccination, and antibody therapy) can be used to suppress ongoing inflammatory diseases such as experimental autoimmune encephalomyelitis (EAE) and Intestinal Bowels Disease (IBD, see Examples 1-5). The present inventors also developed, through laborious experimentations and screening a novel therapeutic anti-SR-B1 monoclonal antibody, E12, which is capable of altering the cytokine profile and inflammatory activities of macrophages. This antibody which is directed against a surface exposed epitope of the scavenger receptor (FIG. 6) is cross-reactive to human CLA-I (human SR-B1) and also affects the cytokine profile and in vitro activities of human macrophages (a cell line) and as such can be used as a valuable therapeutic tool (see Example 6). This antibody was also shown effective in suppressing ongoing EAE and TNBS induced IBD (see Example 7). Immunohistological analysis clearly showed that in both diseases anti SR-BI therapy altered the cytokine production of invading leukocytes, at the autoimmune site, into high IL-10 producing cells. This may explain, significant therapeutic effect of this antibody in these diseases. Immunohistological analysis of CNS sections using anti SR-BI mAb also showed that SR-BI positive leukocytes enter the site of inflammation (so far detected only for EAE). Thus, it is suggested that anti SR-BI antibodies affect the cytokine profile and inflammatory functions of inflammatory leukocytes (mostly monocytes) entering the autoimmune site, and thereby the function and polarization of autoimmune T cells there.

These findings suggest that scavenger receptors can be used as targets for diagnostics and treatment of inflammatory diseases, especially IBD and multiple sclerosis.

Thus, according to one aspect of the present invention there is provided a method of reducing an inflammatory response in a subject.

As used herein the term "reducing" refers to preventing, curing, reversing, attenuating, alleviating, minimizing, suppressing or halting the deleterious effects of an inflammatory response.

As used herein the phrase "inflammatory response" refers to an immune response which results in inflammation, typically occurring as a result of injurious stimuli including infection, burns, trauma, neoplasia, autoimmune signals and exposure to chemicals, heat or cold or any other harmful stimulus. An inflammatory response according to the present invention refers to an acute phase response and a chronic inflammation.

As used herein the term "subject" refers to subject who may benefit from the present invention such as a mammal (e.g., canine, feline, ovine, porcine, equine, bovine, human), preferably a human subject.

The method of this aspect of the present invention is effected by providing to a subject in need thereof a therapeutically effective amount of an agent capable of reducing activity and/or expression of a scavenger receptor or of an effector thereof, thereby reducing the inflammatory response in the subject.

As is described in detail hereinbelow, such an agent can directly reduce activity and/or expression of the scavenger receptor, or alternatively activate endogenous components which in turn reduce activity and/or expression of the scavenger receptor (indirect).

As used herein a "scavenger receptor" refers to a gene product (i.e., RNA or protein) of a scavenger receptor, which is known in the Art. Examples of scavenger receptors include but are not limited to class A scavenger receptors, class B scavenger receptors and class F scavenger receptors. The scavenger receptor is preferably one which is expressed and displayed by macrophages. Preferably, the scavenger receptor of the present invention is SR-BI, a member of the CD36 family, GenBank Accession No. NP_005496, also known as CLA-I or SR-B1.

Scavenger receptor activity refers to cell adhesion activity, transporter activity, apoptotic activity, lipid metabolism activity, signal transduction activity and/or preferably cytokine secretion activity.

An effector of a scavenger receptor refers to an endogenous molecule which up-regulates or activates scavenger receptor activity. For example, an effector can be a modified lipid (e.g., oxidized lipid, glaciated lipid, alkylated lipid, nitrated lipid, acetylated lipid), which binds to the scavenger receptor and activates signaling therefrom.

A number of agents can be used in accordance with this aspect of the present invention to reduce the activity or expression of a scavenger receptor or an effector thereof. Depending on the type of molecule utilized, an agent can either be directly administered to the subject or expressed in cells thereof as is further described hereinbelow.

Thus, for example the agent can be a complementarity-determining region (CDR) containing polypeptide (e.g., a neutralizing antibody) which inhibits the activity of a scavenger receptor [such as by binding to the extracellular collagenous domain of SR which plays a role in ligand binding. See Acton (1993) J. Biol. Chem. 268(5):3530-7] or an effector thereof. Also provided are polynucleotides encoding such CDR containing polypeptides. A scavenger receptor neutralizing antibody is described in Example 6 of the Examples section which follows. Other SR-neutralizing antibodies are known in the art, see for example Frolov (2000) J. Biol. Chem. 275(17): 12769-12780. According to presently known preferred embodiments the neutralizing antibody comprises an antigen recognition domain comprising at least one CDR selected from the group consisting of SEQ ID NO: 23, 24, 25, 26, 27, 28, 29, 30, 31, 32, 33, 34, 35 and 36 (e.g., E12, see Example 6).

The term "antibody" refers to whole antibody molecules as well as functional fragments thereof, such as Fab, F(ab')$_2$, and Fv that are capable of binding with antigenic portions of the target polypeptide. These functional antibody fragments constitute preferred embodiments of the present invention, and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule as described in, for example, U.S. Pat. No. 4,946,778.

Purification of serum immunoglobulin antibodies (polyclonal antisera) or reactive portions thereof can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

Methods of generating and isolating monoclonal antibodies are well known in the art, as summarized for example in reviews such as Tramontano and Schloeder, Methods in Enzymology 178, 551-568, 1989. A recombinant scavenger receptor polypeptide may be used to generate antibodies in vitro (see Example 6 of the Examples section which follows). In general, a suitable host animal is immunized with the recombinant polypeptide. Advantageously, the animal host used is a mouse of an inbred strain. Animals are typically immunized with a mixture comprising a solution of the recombinant polypeptide in a physiologically acceptable vehicle, and any suitable adjuvant, which achieves an enhanced immune response to the immunogen. By way of example, the primary immunization conveniently may be accomplished with a mixture of a solution of the recombinant polypeptide and Freund's complete adjuvant, said mixture being prepared in the form of a water in oil emulsion. Typically the immunization will be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the polypeptide can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multi-well plates, and the culture supernatants are screened to identify cultures containing antibodies that recognize the hapten of choice. Hybridomas that secrete antibodies that recognize the recombinant polypeptide are cloned by limiting dilution and expanded, under appropriate culture conditions. Monoclonal antibodies are purified and characterized in terms of immunoglobulin type and binding affinity.

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, in U.S. Pat. Nos. 4,036,945 and 4,331,647, and references contained therein, which patents are hereby incorporated by reference in their entirety (see also Porter, R. R., Biochem. J., 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al. (Proc. Nat'l Acad. Sci. USA 69:2659-62, 1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, all of which are hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick and Fry Methods, 2: 106-10, 1991).

Humanized forms of non-human (e.g., murine) antibodies are chimeric molecules of immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art (see also Example 6 of the Examples section). Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239: 1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human monoclonal antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

An agent for reducing the activity of a scavenger receptor or an effector thereof can also be a non-functional derivative thereof (i.e., dominant negative). For example, artificial dominant negative molecules of scavenger receptors have been previously described by Acton (1993 Supra. Such truncation mutants lack the positively charged collagenous extracellular domain and while retain trimerization, post-translational processing, intracellular transport, surface expression, and stability, are unable to bind ligand and have a dominant negative effects over wild-type receptors [see also Dejager et al. J Clin Invest. 1993 August; 92(2):894-902].

It will be appreciated that when available, naturally occurring non-functional derivatives of the pathway can be used. Thus, for example, the present invention can use the natural inhibitor of SR-A isoform which modifies ligand uptake [see Gough J Lipid Res. 1998 March; 39(3):531-43].

Polypeptides of these non-functional derivatives can be synthesized using solid phase peptide synthesis procedures which are well known in the art and further described by John Morrow Stewart and Janis Dillaha Young, Solid Phase Peptide Syntheses (2nd Ed., Pierce Chemical Company, 1984). Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the proteins are desired, they can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Alternatively, these proteins can encoded expressed within the target cell from an exogenous polynucleotides ligated into a nucleic acid expression construct.

It will be appreciated that the nucleic acid construct can be administered to the individual employing any suitable mode of administration, described hereinbelow (i.e., in vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

To enable cellular expression of the polynucleotides of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (see Invitrogen's website). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Alternatively, the agent of this aspect of the present invention can be a chemical, which is designed to specifically inhibit the activity or expression of a scavenger receptor or an effector thereof. An example of a scavenger receptor inhibitor is Pitavastatin [NK-104, Circulation. 2004 Feb. 17; 109(6): 790-6], which down-regulates expression of CD36. Further it is well established that TNF-α regulates scavenger receptor expression through MAPK (e.g., ERK, JNK, and p38). Thus it is suggested that short term inhibition of this pathway down-regulates the receptor expression, while long term treatment with TNF-α is expected to have the same effect [Hsu J Biol. Chem. 2000 Dec. 29; 275(52):41035-48]. Signal transduction factors and inhibitors are available from a number of chemical companies including Calbiochem (San Diego, Calif., USA) and Sigma-Aldrich Corp. (St Louis, Mo., USA).

Another agent capable of reducing the expression of an SR or effectors thereof is a small interfering RNA (siRNA) molecule. RNA interference is a two-step process. the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, an SR-B1 mRNA sequence (e.g., GenBank Accession No. NP_005496), for example, is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (see Ambion's website).

Second, potential target sites are compared to an appropriate genomic database (e.g., human, mouse, rat etc.) using any sequence alignment software, such as the BLAST software available from the NCBI server ( ). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation.

For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

One example of a siRNA molecule directed at a SR (i.e., p120) is described by Nishikawa Eur J. Biochem. 2001 October; 268(20):5295-9.

Another agent capable of downregulating a SR or an effector thereof is a DNAzyme molecule capable of specifically cleaving an mRNA transcript or DNA sequence of interest. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther). In another application, DNAzymes complementary to bcr-ab 1 oncogenes were successful in inhibiting the oncogenes expression in leukemia cells, and lessening relapse rates in autologous bone marrow transplant in cases of CML and ALL.

Reducing expression of SR or an effector thereof can also be effected by using an antisense polynucleotide capable of specifically hybridizing with an mRNA transcript encoding the proteins of interest.

Design of antisense molecules which can be used to efficiently downregulate a gene product of interest must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit β-globin (RBG) and mouse tumor necrosis factor-α (TNF-α) transcripts. The same research group has more recently reported that the antisense activity of rationally selected oligonucleotides against three model target mRNAs (human lactate dehydrogenase A and B and rat gp 130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

SR-specific antisense molecules have been previously described by Rhainds Biochemistry. 2003 Jun. 24; 42(24): 7527-38; Zingg Arterioscler Thromb Vasc Biol. 2002 Mar. 1; 22(3):412-7; and Imachi Lab Invest. 2000 February; 80(2): 263-70.

Another agent capable of reducing the expression of scavenger receptor or an effector thereof is a ribozyme molecule capable of specifically cleaving an mRNA transcript encoding this gene product. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

An additional method of reducing the expression of an SR gene or effectors thereof in cells is via triplex forming oligonucleotides (TFOs). Recent studies have shown that TFOs can be designed which can recognize and bind to polypurine/polypyrimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

```
oligo     3'--A     G     G     T
duplex    5'--A     G     C     T
duplex    3'--T     C     G     A
```

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Additional description of oligonucleotide agents is further provided hereinbelow. It will be appreciated that therapeutic oligonucleotides may further include base and/or backbone modifications which may increase bioavailability therapeutic efficacy and reduce cytotoxicity. Such modifications are described in Younes (2002) Current Pharmaceutical Design 8:1451-1466.

For example, the oligonucleotides of the present invention may comprise heterocylic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-

1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

As is mentioned hereinabove the agent according to this aspect of the present invention can be also a molecule, which indirectly causes reduction of SR activity or expression.

An example of such an agent is a molecule which promotes specific immunogenic response to a scavenger receptor or an effector thereof in the subject. Such a molecule can be an SR-BI protein, a fragment derived therefrom or a nucleic acid sequence encoding same (see Examples 1-5 of the Examples section which follows). Although such a molecule can be provided to the subject per se, the agent is preferably administered with an immunostimulant in an immunogenic composition.

An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes into which the compound is incorporated (see e.g., U.S. Pat. No. 4,235,877).

Vaccine preparation is generally described in, for example, M. F. Powell and M. J. Newman, eds., "Vaccine Design (the subunit and adjuvant approach)," Plenum Press (NY, 1995).

Illustrative immunogenic compositions may contain DNA encoding a scavenger receptor, such that the protein is generated in situ. The DNA may be present within any of a variety of delivery systems known to those of ordinary skill in the art, including nucleic acid expression systems, bacteria and viral expression systems. Gene delivery techniques are well known in the art, such as those described by Rolland, Crit. Rev. Therap. Drug Carrier Systems 15:143-198, 1998, and references cited therein.

Preferably, the DNA is introduced using a viral expression system (e.g., vaccinia or other pox virus, retrovirus, lentivirus or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993.

Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

It will be appreciated that an immunogenic composition may comprise both a polynucleotide and a polypeptide component. Such immunogenic compositions may provide for an enhanced immune response.

Any of a variety of immunostimulants may be employed in the immunogenic compositions of this invention. For example, an adjuvant may be included. Most adjuvants contain a substance designed to protect the antigen from rapid catabolism, such as aluminum hydroxide or mineral oil, and a stimulator of immune responses, such as lipid A, Bortadella pertussis or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2,-7, or -12, may also be used as adjuvants.

The adjuvant composition may be designed to induce an immune response predominantly of the Th1 type. High levels of Th1-type cytokines (e.g., IFN-γ, TNF-α, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, the subject will support an immune response that includes Th1- and Th2-type responses. The levels of these cytokines may be readily assessed using standard assays. For a review of the families of cytokines, see Mosmann and Coffinan, Ann. Rev. Immunol. 7:145-173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720.

A delivery vehicle can be employed with the immunogenic composition of the present invention in order to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Dendritic cells are highly potent APCs (Banchereau and Steinman, Nature 392:245-251, 1998) and have been shown to be effective as a physiological adjuvant for eliciting prophylactic or therapeutic antitumor immunity (see Timmernan and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNF-α to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNF-α, CD40 ligand, LPS, flt3 ligand and/or other compound(s) that induce differentiation, maturation and proliferation of dendritic cells.

Dendritic cells are categorized as "immature" and "mature" cells, which allows a simple way to discriminate between two well characterized phenotypes. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a SR, such that SR-BI, or an immunogenic portion thereof, is expressed on the cell surface. Such transfection may take place ex vivo, and a composition comprising such transfected cells may then be used for therapeutic purposes, as described herein. Alternatively, a gene delivery vehicle that targets a dendritic or other antigen presenting cell may be administered to the subject, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the SR polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule) such as described above. Alternatively, a dendritic cell may be pulsed with a non-conjugated immunological partner, separately or in the presence of the polypeptide.

It will be appreciated that selection of agents which are capable of reducing the activity or expression of a scavenger receptor or effectors thereof is preferably effected by examining their effect on at least one of the above-described scavenger receptor activities. Preferably modulation of inflammatory cytokine expression in macrophages, such as described in Example 6 of the Examples section.

The above-described agents for reducing expression or activity of a scavenger receptor or of effectors thereof (i.e., active ingredients) can be provided to the subject per se, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transversal, intestinal or parenteral delivery, including intramuscular, subcutaneous and intramedullary injections as well as intrathecal, direct intraventricular, intravenous, intraperitoneal, intranasal, or intraocular injections. Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch. The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use. The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated. Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

A number of diseases and conditions, which typically cause inflammatory response in individuals can be treated using the methodology described hereinabove. Examples of such diseases and conditions are summarized infra.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8): 1759); autoimmune reproductive diseases, ovarian diseases, ovarian autoimmunity (Garza KM. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante AJ. And Kraig E, Int Rev Immunol 1999; 18 (1-2):83), motor neuropathies (Kornberg AJ. J Clin Neurosci. 2000 May; 7 (3):191), Guillain-Barre syndrome, neuropathies and autoimmune neuropathies (Kusunoki S. Am J Med. Sci. 2000 April; 319 (4):234), myasthenic diseases, Lambert-Eaton myasthenic syndrome (Takamori M. Am J Med. Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine JC. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann NY Acad. Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala 0. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel LH. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta SK., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander RB. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 March 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2): 157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi AP. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth GS. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander RB. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante AJ. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med. Sci. 2000 April; 319 (4):234), myasthenia, Lambert-Eaton myasthenic syndrome (Takamori M. Am J Med. Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly CJ. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

In addition to therapeutic advances pioneered by the present invention, the unprecedented findings that antibodies to scavenger receptor are expressed during an inflammation response may be also employed in diagnostic applications (see Examples 1 of the Examples section which follows).

Thus, according to another aspect of the present invention there is provided a method of diagnosing predisposition to, or presence of, an inflammatory response or diseases related therewith (such as described above) in a subject.

As used herein the term "diagnosing" refers to classifying a disease or a symptom as an inflammatory disease, determining a severity of such a disease, monitoring disease progression, forecasting an outcome of a disease and/or prospects of recovery.

The method is effected by detecting autoantibodies to a scavenger molecule in a biological sample obtained from the subject, wherein a level of the autoantibodies above a predetermined threshold (i.e., the level of the same in a biological sample obtained from a healthy individual) in indicative of the disease in the subject.

As used herein a "biological sample" refers to an antibody-containing sample of cell, tissue or fluid derived from the subject. Antibodies present in the sample are typically found within cytoplasmic membrane-bound compartments (e.g., endoplasmic reticulum and Golgi apparatus) and on the surface of B lymphocytes (which synthesize antibody molecules) and immune effector cells such as, mononuclear phagocytes, natural killer (NK) cells and mast cells, which express specific receptors for binding antibody molecules. Antibodies are also present in the plasma (i.e., fluid portion) of the blood and in the interstitial fluid of the tissues. Antibodies can also be found in secretory fluids such as mucus, synovial fluid, sperm and milk into which certain types of antibody molecules are specifically transported.

Procedures for obtaining biological samples (i.e., biopsying) from individuals are well known in the art. Such procedures include, but are not limited to, blood sampling, joint fluid biopsy, cerebrospinal biopsy and lymph node biopsy. These and other procedures for obtaining tissue or fluid biopsies are described in details in the Health A to Z website.

Regardless of the procedure employed, once the biological sample (i.e., normal and abnormal) is obtained, the titer (number) of antibody molecules for a scavenger receptor in the biological sample is determined.

Antibody titer can determined by techniques which are well known in the art such as ELISA and dot blot using an immobilized antigen (see for Example Abbas, Lichtman and Pober "Cellular and Molecular Immunology". W.B. Saunders International Edition 1994 pages 56-59). Specifically, the antigen is preferably immobilized on a solid support. To avoid non-specific binding of antibodies, the solid support is preferably coated with a nonantigenic protein as well. A peptide is typically immobilized on a solid matrix by adsorption from an aqueous medium, although other modes of immobilization applicable to proteins and peptides well known to those skilled in the art can be used. Useful solid matrices are also well known in the art. Such materials are water insoluble and include cross-linked dextran (e.g., SEPHADEX™, Pharmacia Fine Chemicals, Piscataway, N.J.), agarose, polystyrene beads about 1 µm to about 5 mm in diameter, polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

Once the antigens are immobilized antibody-containing samples are added in serial dilutions until binding can no longer be observed. The antibody containing samples can be either a crude sample or immunoglobulin purified samples (e.g., ammonium sulfate precipitated fraction and/or chromatography isolated). Immunocomplexes are allowed to form and the support is washed to remove non-specifically bound antisera. Detection of immunocomplexes can be effected by adding labeled antibody-binding molecules such as staphylococcal protein A. The label can be an enzyme such as horseradish peroxidase (HRP), glucose oxidase, or the like. In cases where the major indicating group is an enzyme such as HRP or glucose oxidase, additional reagents are required to indicate that an immunocomplex has formed. Such additional reagents for HRP include hydrogen peroxide and an oxidation dye precursor such as diaminobenzidine. An additional reagent useful with glucose oxidase is 2,2,-azino-di-(3-ethyl-benzothiazoline-G-sulfonic acid) (ABTS).

Radioactive labels may also be used in accordance with the present invention. An exemplary radiolabeling agent is a radioactive element that produces γ ray emissions, such as $^{125}$I. Methods of protein labeling are well-known in the art and described in details by Galfre et al., Meth. Enzyol., 73:3-46 (1981). The techniques of protein conjugation or coupling through activated functional groups are also applicable. See, for example, Aurameas et al., Scand. J. Immunol., 8(7):7-23 (1978); Rodwell et al., Biotech., 3:889-894 (1984); and U.S. Pat. No. 4,493,795.

Agents of the present invention (described above) can be included in a diagnostic or therapeutic kit. Thus, for example, antibodies and/or chemicals can be packaged in a one or more containers with appropriate buffers and preservatives and used for diagnosis or for directing therapeutic treatment.

Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added.

The kit can also include instructions for determining if the tested subject is suffering from, or is at risk of developing inflammation.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

SR-B1 Vaccine Suppresses EAE Disease Progression

The effect of SR-B1 vaccination prior to EAE induction in Lewis rats was evaluated by manifestation of EAE clinical symptoms. The produced SR-B1 autoantibodies were used to evaluate the effect of these antibodies on an ongoing disease.

Materials and Methods

Animals:

Female Lewis rats, approximately six weeks old, were purchased from Harlan (Jerusalem, Israel) and maintained under SPF (specific pathogen-free) conditions in the Technion animal facility (Bruce Rappaport Faculty of Medicine, Technion, Haifa, Israel).

Peptide Antigens:

Myelin Basic Protein (MBP) p68-86, Myelin Oligodendrocyte Glycoprotein (MOG) p33-55 were all synthesized on a MilliGen 9050 peptide synthesizer by standard 9-fluorenylmethoxycarbonyl chemistry and purified by high performance liquid chromatography. Sequence was confirmed by amino acid analysis and the correct mass was checked by mass spectroscopy. Peptides with over 95% purity were used.

Immunizations, Active Disease Induction and Disease Score:

Active induction of EAE in each experimental model was done as described before (20, 24, 25). Animals were then monitored for clinical signs daily by an observer blind to the treatment protocol. EAE was scored as follows: 0, clinically normal; 1, flaccid tail; 2, hind limb paralysis; 3, total hind limb paralysis, accompanied by an apparent front limb paralysis; 4, total hind limb and front limb paralysis.

DNA Vaccines:

A plasmid DNA vaccine-encoding SR-B1 was prepared as described before (10). In brief, RNA extracted from EAE brains of Lewis rats was subjected to RT-PCR using oligonucleotide primers [sense 5'-CCATGGGCGGCAGCTC-CAGGGC-3' (SEQ ID NO: 1), anti-sense 5'-CTACAGCT-TGGCTTCTTGCAC-3' (SEQ ID NO: 2)] complimentary to the published sequence of SR-B1 (Accession No: AF071495). This RT-PCR reaction mixture was subjected to an amplification program of 1 min at 95° C., 1 min at 55° C. and 1 min at 72° C. for 25 cycles. The 1.53 kb amplified product (SEQ ID NO:3) comprising nucleotides 10-1539 of SRB1R from *Rattus norvegicus* (Accession No: AF071495), was loaded onto a 5% polyacrylamide gel in TAE buffer, gel purified, sequenced and then ligated into a pcDNA3 plasmid. Prior to its use as a vaccine, the construct was injected to tibia muscle of rats that were sacrificed at different time points and the expression of RNA encoding SR-B1 was verified. Under the working condition of the present study, SR-B1 was highly transcribed in the leg muscle for not more than 25 days. DNA vaccines were administrated at a dose of 100 µg plasmid in 1000 PBS to the to tibia muscle.

Production and Purification of Recombinant SR-B1:

PCR product of SEQ ID NO: 3 was re-cloned into a PQE expression vector (Qaigen, Chatsworth, Calif.), expressed in *E. coli* and then purified by an NI-NTA-supper flow affinity purification of 6×His proteins (Qaigen, Chatsworth, Calif.). After purification, the purity of recombinant SR-B1 was verified by gel electrophoresis followed by N-terminus sequencing (Protein Services Unit of the Technion, Haifa, Israel).

Evaluation of Anti SR-B1 Antibody Titer in Sera of Vaccinated Rats:

A direct ELISA assay has been utilized to determine the anti SR-B1 antibody titer in DNA vaccinated rats. ELISA plates (Nunc, Roskilde, Denmark) were coated with 50 ng/well of the recombinant SR-B1 protein produced in the present study as described above, Sera from DNA vaccinated rats were added in serial dilutions from $2^5$ to $2^{30}$ to wells that were, or were not, coated previously with recombinant SR-B1. Calculation of each titer was done by comparing the O.D. measured (405 nm) in wells coated with SR-B1 to those not coated with this recombinant gene product. Goat anti-rat alkaline phosphatase conjugated IgG antibodies (Sigma) were used as a labeled antibody. p-Nitrophenyl Phosphate (p-NPP) (Sigma) was used as a soluble alkaline phosphatase substrate. Results were collected by ELISA reader (TECAN Spectra rainbow thermo absorber mini-plate reader). Results of triplicates were calculated as $\log_2$Ab titer±SE.

Evaluation of Anti β-Actin Antibody Titer in Sera of Vaccinated Rats:

Recombinant soluble β-actin was obtained as described before (11). In brief, cDNA encoding rat β-actin (the natural cytoplasmic soluble form of β-actin, GenBank Accession NO: NM_031144) was PCR amplified using specific oligonucleotide primers [sense 5'-ATGGATGACGATATCGCT-GCGCTC-3' (SEQ ID NO:4); anti-sense 5'-CTACCGGC-CAGCCAGACG-3' (SEQ ID NO:5)]. Following cloning and sequence verification, the above cDNA was ligated into the pcDNA3 vector to be used as a control DNA vaccine). ELISA test was conducted as described above, but ELISA plates were coated with soluble β-actin rather than recombinant SR-B1.

IgG Purification:

IgG was purified as described before (11).

Anti SR-B1 Specific Antibody Purification:

Recombinant rat SR-B1 (5 mg) encoded by SEQ ID NO:3, was bound to a CNBr activated Sepharose Column according to the manufactures instructions (Pharmacia biotech, catalog number 17-0820-01). Anti SR-B1 specific antibodies from sera (IgG fraction) of DNA vaccinated rats were loaded on the column and then eluted by an acidic elution buffer (glycine PH 2.5). Isotype of the purified antibody was determined by an ELISA assay in which anti rat IgG1a, IgG2b and IgG1 (Jackson, USA) were used as detection antibodies. Purified antibody was mostly of the IgG2a Isotype (data not shown).

FACS Analysis:

Murine peritoneal macrophages [obtained as described elsewhere (9)], were activated with LPS (1 µg/ml), washed once in FACS buffer (PBS, 0.25% BSA, 0.05% sodium azide), and then incubated for 0.5 hours in FACS buffer enriched with 1% normal rat serum. Cells were then resuspended (4° C., 0.5 hours) in 96-well U plates ($10^6$/well) with 10 µL FACS buffer supplemented with 0.5 µg/ml of IgG purified from rats that were subjected to SR-B1 DNA plasmid administration (anti SR-B1), IgG purified from EAE rats treated with β-actin encoding DNA (control IgG) or no antibodies (no Ab). Cells were then washed with FACS buffer three times and incubated (4° C., 0.5 hours) with 50 µL of FACS buffer supplemented with Goat anti-rat IgG-FITC (#F6258, 1:10,000 dilution; Sigma Chemical Co.). After incubation cells were washed with FACS buffer twice and analyzed in the presence of propidium iodide (PI) using a FACScalibur (Becton Dickinson, Mountain View, Calif., USA). Data was collected for 10,000 events and analyzed using a Cell Quest program (Becton Dickinson).

Statistical and Graphical Methods:

Significance of differences was examined using Student's t-test. A value of P<0.05 was considered significant. Mann-Whitney sum of ranks test was used to evaluate significance of differences in mean of maximal clinical score with P<0.05 considered significant.

Results

The Effect of SR-B1 Injections on EAE Development:

In the first set of experiments, Lewis rats were subjected to four weekly administration of plasmid DNA encoding SR-B1, plasmid DNA encoding β-actin (as positive control), or PBS. Two months after last immunization EAE was induced. The rats treated with plasmid DNA encoding rat SR-B1 (opened triangles) developed a significantly reduced form of disease versus PBS treated rats (closed squares) (FIG. 1a, mean maximal score 3±0.28 Vs 1±0.28. p<0.001). DNA vaccine encoding soluble β-actin had no effect on disease manifestation (FIG. 1a, opened squares). At the peak of disease anti SR-B1 specific antibody titer was determined in all groups (FIG. 1b). Control EAE rats displayed a significant titer against SR-B1 (FIG. 1b $\log_2$Ab titer of 10±0.4 Vs 6±02 in naïve rats, p<0.05) that continued to persist till 6 days after recovery, and then regressed back to background levels (not shown). DNA plasmid encoding SR-B1 dramatically amplified this titer ($\log_2$Ab titer of 22±0.86, p<0.001 as compared to each control group) to provide antibody mediated protective immunity (FIG. 1d). EAE rats did not develop a notable antibody titer to soluble β-actin and DNA plasmid encoding this gene product could not breakdown tolerance against self (FIG. 1b). SR-B1 autoantibodies were found capable of specific binding to the recombinant SR-B1 (FIG. 1b), as well as to the natural form of SR-B1 on activated macrophages (FIG. 1c) and HEK293 line cells transfected with rat SR-B1 (not shown). These autoantibodies could also adoptively transfer EAE resistance to other rats (FIG. 1d, mean maximal score of 3.3±0.3 in control rats Vs 1.66±0.18, p<0.01).

Example 2

The Anti-Inflammatory Mechanism of Anti SR-B1 Antibodies

The mechanism of action of anti SR-B1 antibodies was evaluated by testing their ability to modify cytokine production by murine peritoneal macrophages.

Material and Methods

Murine Peritoneal Macrophages:

Murine peritoneal macrophages were isolated as described before (9). Cells were then activated in vitro with 1 µg/ml LPS for 48 in the presence of (0, 10, 50 and 100 µg/ml) anti SR-B1 polyclonal autoantibodies (CNBr purified, as described in Example 1 of the Examples section), or control IgG from normal rat serum (purified as described in Example 1 of the Examples section).

Cytokine Determination:

Levels of IL-12, TNF-α and IL-10 were determined by ELISA (TECAN Spectra rainbow thermo absorber miniplate reader) using commercially available kits: mouse IL-12 (R&D system Inc. Minneapolis, Minn.), TNF-α & IL-10 (Diaclone, Besancon, France).

Statistical and Graphical Methods:

Statistical methods were as described in Example 1 of the Examples section.

Results

The mechanism of action of anti SR-B1 Antibodies:

To explore the mechanistic basis by which anti SR-B1 antibodies affect the function of the immune system, these antibodies were purified and added to freshly isolated peritoneal macrophages that were activated in vitro with LPS. The presence of anti SR-B1 antibodies in the peritoneal macrophages culture effectively suppressed IL-12 and TNF-α production (FIG. 2a and FIG. 2b, closed squares) and at the same time induced IL-10 production (FIG. 2c, closed squares) as compared to control IgG (FIG. 2, open squares), all in a dose dependent manner (FIG. 2). Thus anti SR-B1 antibodies redirect the polarization of macrophages from a pro-inflammatory to anti-inflammatory mediators.

Example 3

SR-B1 Vaccine Suppresses an Ongoing EAE

The effect of SR-B1 vaccine on an ongoing disease was evaluated by EAE C57BL/6 mice vaccination with plasmid DNA encoding SR-B1, 12 days after onset of the disease.

Materials and Methods

Animals:

C57BL/6 mice, approximately six weeks old, were purchased from Harlan (Jerusalem, Israel) and maintained under SPF conditions in the Technion animal facility (Bruce Rappaport Faculty of Medicine, Technion, Haifa, Israel).

EAE Induction:

EAE was induced according to Semi-chronic model of MOG induced EAE in the C57BL/6 mice as described before (20).

DNA Vaccines:

SR-B1 plasmid DNA vaccine was prepared as described in Example 1 of the Examples section.

Mouse Vaccination:

12 days after the induction of EAE (1-2 days after its onset) sick mice were separated into 3 group of 6 C57BL/6 mice that were subjected to either a single administration of plasmid DNA encoding SR-B1 (pcDNA3-SR-B1), a single administration of pcDNA3 (empty vector), or no injection (control). Vaccination was effected by administration of 100 µg plasmid in 1000 PBS as described Example 1 of the Examples section.

Statistical and Graphical Methods:

Statistical analysis was effected as described in Example 1 of the Examples section.

Results

The effect of SR-B1 injections on the dynamics of an ongoing EAE disease:

Semi-chronic model of MOG induced EAE in the C57BL/6 mice (20) was used to evaluate the effect of a plasmid DNA vaccine encoding SR-B1 on the dynamics of an ongoing EAE disease (FIG. 3). At this time anti SR-B1 specific antibody titer excited the level of $\log_2$Ab titer of 11±0.4 (Vs 6±0 in naïve mice) this titer accelerated to $\log_2$Ab titer of 21±0.66 in SR-B1 encoding DNA treated mice ($p<0.001$) (Data not shown). This acceleration was followed by a fast entry to remission in treated mice (FIG. 3, $p<0.001$). These data further suggest that SR-B1 encoding DNA vaccine amplifies a pre-existing regulatory response.

Example 4

Anti SR-B1 Monoclonal Antibodies Suppress Ongoing EAE

Anti SR-B1 monoclonal antibody was produced, and tested for its ability to modulate cytokine production by peritoneal activated macrophages as well as to affect an ongoing EAE disease Materials and Methods Production of Monoclonal Anti SR-B1 Antibody:

C57/B6 mice were subsequently immunized (3 weekly immunizations) with the SR-B1 encoding DNA plasmid. Two weeks after the last administration, these mice were subjected to active induction of EAE. Spleen cells were obtained for production of monoclonal antibodies two weeks later with SP2 cells (ATCC) as a fusion partner as described before (E. Harlow & D. Lane, Antibodies, Cold Spring Harbor Laboratory Press, 1998). Screening of positive hybridoma was done in two steps of selection. The first one selected positive antibodies producing cells according to the ability to bind SR-B1 over expressed by HEK293. Supernatant isolated from hybridoma clones (1000 wells) was then subjected to FACS analysis for their ability to bind SR-B1.

Antibodies and Peritoneal Macrophages:

Peritoneal macrophages were obtained from thioglycollate (25%, 3 ml) injected C57BL/6 mice and co-cultured with 1 µg/ml LPS for 48 in the presence, or absence, of anti SR-B1 polyclonal antibody (1:100, Calbichem, San Diego, Calif.), the monoclonal anti SR-B1 antibody generated as described above (Clone 5D8, 10 µg/ml), isotype matched control antibody (IgG1$_\kappa$, Sigma), HDL (Chemicon International Temecula, Calif.) or anti murine CD36 (5 µg/ml, Santa Cruz Biotechnology, Santa Cruz, Calif.). Cytokine levels were determined by ELISA as described in Example 2 of the Examples section. Results are shown as mean triplicates±SE.

Antibodies Administration to EAE Rats:

Lewis rats were subjected to active EAE as described in Example 1 of the Examples section. 1-2 days after the onset of disease these Lewis rats (6 in each group) were treated, every other day, with 100 µg/ml of monoclonal antibody 5D8 (anti SR-B1 monoclonal antibody selected from hybridoma, as described above, which recognizes the murine homolog of SR-B1), control murine IgG1 (Sigma), anti SR-B1 polyclonal antibody (produced as described in Example 1 of the Examples section), control rat IgG2a purified from EAE rats that have been subjected to an empty plasmid DNA vaccination or PBS. Data was obtained by an observer blind to the experimental protocol as described in Example 1 of the Examples section. Results are presented as mean maximal score±SE.

Results
The Effect of Monoclonal Antibody to SR-B1 on Cytokine Production of LPS Activated Peritoneal Macrophages:

The ability of anti SR-B1 specific monoclonal antibody to alter the cytokine profile produced by peritoneal macrophages and by the murine monocyteric cell line J774 (ATCC) was evaluated by their cytokines expression. Table 1 compares the competence of one of these antibodies (clone 5D8, IgG1) to decrease TNF-α and increase IL-10 production by LPS activated murine peritoneal macrophages to the effect of commercially available polyclonal antibody to SR-B1, to CD36 and to HDL. Each response was optimized during a preliminary experiment in which different doses were determined for properties to affect these parameters.

TABLE 1

The effect of anti SR-B1 monoclonal antibody on cytokine production of LPS activated peritoneal macrophages

| Treatment | TNF-α (pg/ml) | IL-10 (pg/ml) |
| --- | --- | --- |
| — | 3280 ± 210 | 730 ± 80 |
| Anti SR-B1 (polyclonal) | 1760 ± 190 | 1240 ± 160 |
| Anti SR-B1 (clone 5D8) | 1640 ± 140 | 1630 ± 150 |
| Control murine IgG1$_\kappa$ | 3350 ± 260 | 710 ± 100 |
| HDL (100 μg/ml) | 2560 ± 130 | 146 ± 30 |
| Anti CD36 (polyclonal) | 4660 ± 330 | 330 ± 90 |

The anti SR-B1 monoclonal antibody produced by spleen cells isolated from the mice treated with SR-B1 encoding DNA vaccine and the anti SR-B1 specific polyclonal antibody could both suppress TNF-α production (1640±140 and 1760±190 pg/ml Vs 3280±210 pg/ml in control samples, p<0.001, Table 1). Control IgG1$_\kappa$ (Sigma) had no significant effect on the production of these cytokines (Table 1). Very similar results were obtained using the murine monocyteric cell line J774 or peritoneal macrophages from rats (data not shown). HDL could reduce TNF-α production (2560±130 Vs 3280±210, p<0.05) but also decreased the production of the anti-inflammatory cytokine IL-10 (Table 1). Anti CD36 antibodies markedly increased TNF-α production (Table 1, p<0.01).

The Effect of Anti SR-B1 Monoclonal Antibody on EAE:

The ability of the isolated anti SR-B1 monoclonal antibody to suppress EAE was evaluated in adoptive transfer experiments. The antibodies were transferred to EAE rats just after the onset of disease and led to a significant reduction in disease severity (mean maximal score of 1.66±0.2 in treated rats Vs 3±0.3 in control rats, p<0.05, FIG. 4).

Example 5

Anti SR-B1 Antibodies Suppress an Ongoing Inflammatory Bowel Disease (IBD)

Anti SR-B1 antibodies were used to treat an induced IBD in Lewis rats.

Materials and Methods
Animals:
Female Lewis rats, approximately six weeks old (120-150 g), were maintained as described in Example 1 of the Examples section.

Induction of Colitis:
Experimental colitis was induced by intrarectal instillation of 250 μl of 125 mg/ml 2,4,6-trinitrobenzene sulfonic acid (TNBS) solution (Fluka, cat#92822) dissolved in 50% ethanol, using 8 cm neonate feeding tube as described before [Fiorucci, S. et al., Immunity, 17:769., 2002]. 24 hours post injection all rats developed bloody diarrhea and severe diarrhea in the next day, accompanied with continuous loss of weight.

Anti SR-B1 and IgG Antibodies:
Specific anti SR-B1 polyclonal antibodies and IgG antibodies were purified as described in Example 1 of the Examples section.

Rat Vaccination:
5 days after the induction of IBD, when the clinical manifestation of disease was apparent in all rats, they were separated into 3 groups of 6 equally sick rats each. On days 6, 8 and 10 after induction of disease these groups were administered with either rat anti SR-B1 polyclonal antibodies (DNA vaccination based antibody, produced as described in Example 1 of the Examples section, 100 μg/rat in PBS), rat IgG from pre-immunized rats (100 μg/rat in PBS), or PBS (control).

Histological Sections:
Histological sections were conducted according to Fiorucci et al., [Fiorucci, S., et al., Immunity 17:769, 2002]. Briefly, on day 15 post induction of colitis, Lewis rats were sacrificed and colons (cecum to rectum) were extracted, flushed with PBS and fixed in NBF (neutral buffered formalin). Paraffin sections (6 μm) were made and stained with H&E (hematoxylin and eosin). Each section represents ~250 sections that were screened by an observer blind to the experimental protocol.

Results
Diarrhea Symptoms:
On day 15, post induction of the colitis, all 6 rats treated with anti SR-B1 showed no signs of diarrhea and solid feces could be seen in the cage. Control rats (positive control of PBS treated rats and rats treated with control IgG) suffered from severe diarrhea with no solid feces in the cage.

Histological Sections of Rats Colons:
Histological colon sections of untreated rats showed normal mucosa with well defined colonic crypts and glands. Histological colon sections of both control rats (positive control of PBS treated rats and rats treated with control IgG) taken 15 days post induction of colitis, showed severe signs of inflammation, megacolon, and signs of perforations (FIGS. 5b-c). Positive control of PBS treated rat sections showed diffuse, mononuclear inflammatory infiltrates in the mucosa and lamina propria, submucosa, and muscularis mucosae (FIG. 5b). Sections displayed various degrees of damage to colonic tissue, ranging from heavily infiltrated areas with epithelial exfoliation to lesions with total destruction of mucosal surface, transmural infiltration, necrosis, and loss of tissue architecture. The control IgG colon sections showed massive destruction of colonic tissue with vast necrotic areas, absence of glandular structure and complete loss of tissue architecture (FIG. 5c). Congestion and edema and congestion were seen in and around blood vessels. Damage was continuous from rectum and extended proximally up to cecum (FIG. 5c). Histological colon sections of rats treated with anti SR-B1 antibodies showed very little signs of inflammation, no perforations, and smaller and paler colons (FIG. 5d). Sections showed moderate inflammatory infiltration, compared to control IgG treated rats (FIG. 5d Vs. FIG. 5c). Although infiltrated, colonic mucosa seems intact with visible brush border and glands and no transmural infiltrates. Submucosa was also much less infiltrated with no wall thickening (FIG. 5d).

These results indicate that treatment of IBD with anti SR-B1 antibodies effectively reduces diarrhea symptoms through reduction of damage to the colon.

Example 6

Therapeutic Monoclonal Human Anti SR-B1 Antibody

A monoclonal human anti SR-B1 antibody was produced for therapeutic use.

Materials and Methods

SR-B1 Encoding Plasmids:

DNA encoding human SR-B1 (CLA-I) was amplified using sense primer: 5' CCATGGGCTGCTCCGCCAAA 3' (SEQ ID NO: 6), and anti-sense primer: 5' CTACAGTTTTGCTTCCTGCAG 3' (SEQ ID NO: 7) The above described reaction mixture was subjected to an amplification program of 1 min at 95° C., 1 min at 55° C. and 1 min at 72° C. for 25 cycles, generating 1.53 kb DNA fragment of SEQ ID NO:8 (*Homo sapiens* encoding SR-B1 mRNA, nucleotides 70-1599 from accession number:Z22555). After PCR reaction, the mixture was loaded onto a 5% polyacrylamide gel in TAE buffer. PCR product was gel-purified, cloned into a pUC57/T vector (T-cloning kit K1212; MBI Fermentas, Vilnius, Lithuania) and then used to transform *E. coli* cells. Clones were then sequenced (Sequenase version 2; Upstate Biotechnology, Cleveland, Ohio) and transferred into a pcDNA3 vector (Invitrogen, San Diego, Calif.). Large-scale preparation of plasmid DNA was conducted using Mega prep (Qiagen, Chatsworth, Calif.).

Cells:

HEK293 (ATCC) were transfected with human SR-B1 as described before [Scarselli E, et al., EMBO J. 21(19):5017-25, 2002]. Expression was verified by FACS analysis as described before [Scarselli E, et al., EMBO J. 21(19):5017-25, 2002].

Production of Monoclonal Human Anti SR-B1 Antibody:

Human anti SR-B1 monoclonal antibodies were produced according to one of the two following protocols:

Protocol I

C57/B6 mice were subsequently immunized (3 weekly immunizations) with the human SR-B1 (SEQ ID NO:8) encoding DNA plasmid. Two weeks after the last administration, these mice were subjected to active induction of EAE. Spleen cells were obtained for production of monoclonal antibodies two weeks later with SP2 cells (ATCC) as a fusion partner as described before (E. Harlow & D. Lane, Antibodies, Cold Spring Harbor Laboratory Press, 1998). Screening of positive hybridoma was done in two steps of selection. The first one selected positive antibodies producing cells according to the ability to bind the recombinant SR-B1 over expressed by HEK293. Supernatant isolated from hybridoma clones (1000 wells) was then subjected to FACS analysis for their ability to bind SR-B1

Protocol II

The cloned human SR-B1 (SEQ ID NO:8), obtained as described above, was re-cloned into a pQE expression vector, expressed in *E. coli* (Qiagen) and then purified by an NI-NTA-supper flow affinity purification of 6×His proteins (Qiagen). After purification, the purity of the recombinant human SR-B1 was verified by gel electrophoresis followed by sequencing (N terminus) by the Technion's sequencing services unit (Technion, Haifa, Israel). This recombinant human SR-B1 was then injected into 10-weeks old BALB/C mice. First immunization was of 50 μg peptide emulsified in CFA [incomplete Freund's adjuvant (IFA) supplemented with 10 mg/ml heat-killed *Mycobacterium tuberculosis* H37Ra in oil; Difco Laboratories, Detroit, Mich.] at a total volume of 400 μl into the peritoneal cavity. Later on, in a 3 weeks interval these mice were administrated with 50 μg/4000 μl or recombinant human SR-B1 emulsified in IFA (Difco Laboratories, Detroit, Mich.). Three weeks after the third interval mice were injected (intravenous) with 50 μg of recombinant human SR-B1 in 100 μl PBS. Three days later spleen cells were obtained and preparation of monoclonal antibodies was conducted as described above.

ELISA—

The indirect ELISA was used to screen hybridomas for antibodies against SR-BI, as follows. Ninety six-well microtiter plates (NUNC) were coated with 50 ng/ml of immuno (recombinant) SR-BI (SEQ ID NO: 8) in phosphate buffered saline (PBS) overnight at 4° C., followed by blocking with 200 μl of 5% BSA in PBS. Then 100 μl of hybridoma supernatants were added and incubated for 1 hr at room temperature (RT). The plates were washed 4 times with PBS containing 0.05% Tween 20 (PBS-T), and then supplemented with peroxidase-conjugated goat anti-mouse IgG antibody for 1 hr at RT, and washed 5 times with PBS-T. Then 100 μl of substrate solution 3,3',5,5'-tetramethyl Benzedrine liquid (ICN biomedical INC, Germany, TMB) were added. The reaction was stopped using 2.5M $H_2SO_4$ and the absorbance was read by an ELISA reader at a wavelength of 450 nm and background of 630 nm.

Cell Binding Assay—

HEK 293 cell line was stably transfected with pcDNA encoding SR-BI (pcSR-BI). Positive clones were selected using neomycin (G418). The positively isolated ELISA hybridoma clones (isolated as described above) were taken into the second screen. Ninety six well disposable flexible polyvinyl chloride microtitration plates (Dynatech laboratories, Virginia) were seeded with $1*10^6$ pcSR-BI-expressing HEK 293 cells. The cells were washed twice with PBS before 100 μl of hybridomas supernatants were added for 30 minutes on ice. Following 3 washes with PBS, peroxidase-conjugated goat anti-mouse IgG antibody was added for additional 20 min on ice. Following 3 washes with PBS 100 μl of substrate solution (TMB) was added. The reaction was stopped using 2.5M $H_2SO_4$. After a short centrifugation, the reaction was transferred into a clean well and the absorbance was read by an ELISA reader at a wavelength of 450 nm and background of 630 nm.

Example 7

In Vitro Characterization of Anti SR-BI Therapeutic Antibodies

Human SR-B1 cross-reactive antibodies (with CLA-I) generated as described in Example 6 according to protocol 2 were in-vitro screened and characterized. The most successful antibody obtained was E12, which was further in-vitro characterized as further described hereinbelow.

Materials and Experimental Procedures

Immunoblot analysis—

For single-label immunohistochemistry, standard methodology was used whereby sections were incubated with primary antibodies (1:100), followed by incubation with secondary antibodies (1:100). Mouse IgG and rabbit polyclonal IgG were used as control antibodies Isotype Analysis—

Isotype analysis was done using Serotec kit (AbD Serotec, Raleigh, N.C., USA).

Culture of peritoneal macrophages—Resident macrophages were obtained from a peritoneal lavage with PBS. Elicited macrophages were harvested 5 days following i.p. injection of 3 ml of 3% Thioglycollate (TG, Difco, Livonia, Mich.). Peritoneal exudate cells were washed, re-suspended in RPMI 1640 medium supplemented with 10% FCS, 1% penicillin, 1% streptomycin, and incubated in 24 flat-bottom plates (10⁶ cells per well in 1 ml) for overnight at 37° C. Nonadherent cells were then removed by vigorous washing (three times), and macrophages monolayers were incubated for 1-10 days in antibiotic-free RPMI containing 10% FCS. Fresh medium was provided every 3 days.

IL-10 Production by Macrophage Culture.

The peritoneal macrophages generated as described above were treated with mAb E12 with or without 0.5 µg/ml LPS (Sigma) for 24 hr at 37° C. Supernatants from either treated or untreated macrophages were assayed for the presence of IL-10 or using immunoenzymatic ELISA kits (Biolegend).

Nitrite Production by Macrophage Culture—

Nitrite formation measurement was done according as described by [Katakura, T., M. Miyazaki, M. Kobayashi, D. N. Herndon, and F. Suzuki. (2004). CCL17 and IL-10 as effectors that enable alternatively activated macrophages to inhibit the generation of classically activated macrophages. J Immunol 172:1407]. Peritoneal macrophages (1*10⁶/ml) were seeded in 24-well plates as describe above. Following treatment with LPS and/or mAb E12 the supernatant was taken and NO production was assayed by measuring the accumulation of nitrite in the culture medium by Griess reaction using Griess reagent system kit (Promega). Briefly: an equal volume of Griess reagent (Sulfanilamide Solution) and macrophage supernatants was incubated for 10 min at RT in a dark room. An equal volume of N-1-napthylethylenediamine dihydrochloride (NED) was then added for 10 min. An ELISA reader measured the absorbance at 550 nm. Nitrite concentration was determined using NaNO₂ as a standard.

Results

Isotype analysis of E12 revealed it to be IgG1. The purified E12 was reacted with a nitrocellulose membrane containing various recombinant proteins. As shown in FIG. 6, mAb E12 cross reacted with SR-BI and CLA-1 but not with MIP, CXCL6 or IL-27. These results indicate that the antibody specifically recognizes scavenger B1 receptor in a cross-species dependent manner and is capable of recognizing the denatured form of the protein indicating that it is directed against an exposed epitope of the native protein, as further demonstrated by its ability to neutralize SR-B1 activity.

The ability of E12 to neutralize SR-B1 signaling, was in vitro assayed on cultured peritoneal macrophages. As shown in FIG. 7 cultured peritoneal macrophages treated for 24 hours with 0.5 µg/ml LPS and with mAb E12, or with isotype matched control IgG, produced significantly higher IL-10 in the presence of increasing amounts of E12 than compared to control treated cells.

These results were substantiated when following NO levels in the presence of E12 antibody and LPS (0.5 µg/ml). As shown in FIG. 8, mAb E12 suppressed NO synthesis (as determined by nitrite levels) by peritoneal macrophages in a dose dependent manner. Control matched isotypes had no effect of NO levels.

The variable regions of E12 heavy chain (VH) and light chain (VK) were sequenced and their CDR composition determined. SEQ ID NO: 9 and 10 show the amino acid and nucleic acid sequences of framework 1 (FWR1) of E12 light chain, respectively. SEQ ID NO: 11 and 12 show the amino acid and nucleic acid sequences of CDR1 of E12 light chain, respectively. SEQ ID NO: 13 and 14 show the amino acid and nucleic acid sequences of framework 2 (FWR2) of E12 light chain, respectively. SEQ ID NO: 15 and 16 show the amino acid and nucleic acid sequences of CDR2 of E12 light chain, respectively. SEQ ID NO: 17 and 18 show the amino acid and nucleic acid sequences of framework 3 (FWR3) of E12 light chain, respectively. SEQ ID NO: 19 and 20 show the amino acid and nucleic acid sequences of CDR3 of E12 light chain, respectively. SEQ ID NO: 21 and 22 show the amino acid and nucleic acid sequences of framework 4 (FWR4) of E12 light chain, respectively.

SEQ ID NO: 23 and 24 show the amino acid and nucleic acid sequences of framework 1 (FWR1) of E12 heavy chain, respectively. SEQ ID NO: 25 and 26 show the amino acid and nucleic acid sequences of CDR1 of E12 heavy chain, respectively. SEQ ID NO: 27 and 28 show the amino acid and nucleic acid sequences of framework 2 (FWR2) of E12 heavy chain, respectively. SEQ ID NO: 29 and 30 show the amino acid and nucleic acid sequences of CDR2 of E12 heavy chain, respectively. SEQ ID NO: 31 and 32 show the amino acid and nucleic acid sequences of framework 3 (FWR3) of E12 heavy chain, respectively. SEQ ID NO: 33 and 34 show the amino acid and nucleic acid sequences of CDR3 of E12 heavy chain, respectively. SEQ ID NO: 35 and 36 show the amino acid and nucleic acid sequences of framework 4 (FWR4) of E12 heavy chain, respectively.

Blast analysis of E12 light chain sequence showed no homology to anti SR-B1 antibodies which sequence is available to date. Closest homology was as follows:

1. A set of closely related antibodies which dominate the primary antibody response to the antigenic site CB of the A/PR/8/34 influenza virus hemagglutinin;

2. anti-cocaine monoclonal antibody K1-4 light chain variable region;

3. ANA immunoglobulin kappa light chain [*Mus musculus*]; and 4. anti-GBM [Anti-Glomerular Antigen Antibody-Producing Cells in the Kidneys of MRL/MpJ-Fas (1pr) Mice] immunoglobulin kappa chain variable region [*Mus musculus*].

Example 8

A Monoclonal Antibody to SR-BI is Capable of Suppressing Ongoing EAE and IBD

The monoclonal antibody generated as taught in Example 6 above was shown highly effective in suppressing ongoing EAE and TNBS induced IBD, as further described hereinbelow.

Materials and Methods

Induction of EAE in Mice and Suppression of the Ongoing Disease with mAb to SR-B1—

A group of 18 C57BL/6 mice was subjected to MOGp35-55 induced EAE. At the onset of disease (day 13) these mice were separated into three equally sick groups. On this day and on days 15 and 17 these groups were intravenously administered with 500 µg E12 mAb, isotype matched human IgG (IgG1), or PBS and followed for clinical manifestation of disease (FIG. 9) by an observer blind to the experimental protocol.

Spinal Cord Histopathology—

Histological examination of H&E-stained sections of formalin-fixed, paraffin-embedded sections of the lower thoracic and lumbar regions of the spinal cord was performed. Each section was evaluated without knowledge of the treatment status of the animal. The following scale was used: 0, no mononuclear cell infiltration; 1, one to five perivascular lesions per section with minimal parenchymal infiltration; 2, five to 10 perivascular lesions per section with parenchymal infiltration; and 3, >10 perivascular lesions per section with extensive parenchymal infiltration. The mean histological score±SE was calculated for each treatment group Immunohistochemistry—

For single-label immunohistochemistry, standard methodology was used whereby sections were incubated with primary antibodies (1:100), followed by incubation with secondary antibodies (1:100). Mouse IgG and rabbit polyclonal IgG were used as control antibodies Induction of Experimental Colitis in Lewis Rats—
See Example 5.
Treatment Protocol for Antibody Transfer—
On days 6, 8 and 10 post induction of experimental colitis, 500 µg of mAb E12 was injected intravenously via a tail vein. Human IgG1 (Sigma) was used as a control antibody.

Sample Collection—
On day 12, the rats were killed under ketamine-xylasine anesthesia. The terminal colon was then stripped, gently washed with PBS, opened longitudinally and macroscopically evaluated according to a modification of the criteria described by Morris Gut (2004); 53; 99-107. Colonic injury was scored on a 0 (normal colon) to 5 (severe damage) scale, (see Table 2, below).

Colon Histopathology—
Tissues (terminal colon, mesentery lymph nodes and spleens) were fixed in 10% neutral buffered formalin and embedded in paraffin. Hematoxylin and eosin stained sections of the colon were evaluated histologically for four parameters: extent of ulceration, submucosal infiltration, crypt abscesses and wall thickening (see Table 3). The sum of all scores determined a rating of slight to severe colonic inflammation.

Immunohistochemistry—
Serial sections from formalin-fixed, paraffin-embedded specimens were deparaffinized and rehydrated in decreasing concentrations of ethyl alcohol. Tissue sections were incubated with fresh 3% $H_2O_2$ in methanol for 10 min and then washed with PBS. Sections were then treated by microwave for 15 min in 90° C. in citrate buffer and blocked with 10% donkey serum for 30 min. Immunoistochemical analysis was carried out using primary antibodies against rat IL-10 (polyclonal goat anti rat IL-10, R&D), CD3 (mAb mouse anti rat, Pharmingen) and ED1 (mAb mouse anti rat, Serotec) over night at 4° C. in a humidified chamber. Biotinylated donkey anti goat or anti mouse IgG were used as secondary antibodies, followed by a streptavidin-horseradish peroxidase (Zymed). The reaction was developed using aminoethylcarbazole substrate kit (Zymed).

TABLE 2

Macroscopic assessment of colonic damage

| Macroscopic damage | Score |
| --- | --- |
| No damage | 0 |
| Hyperemia but no ulcers | 1 |
| Fibrosis but no ulcers | 2 |
| Ulceration/necrosis <1 cm | 3 |
| Ulceration/necrosis <2 cm | 4 |
| Ulceration/necrosis >2 cm | 5 |

TABLE 3

Microscopic assessment of colonic inflammation

| Histological appearance | Score |
| --- | --- |
| Extent of ulceration | |
| No ulcer | 0 |
| Small ulcers (<3 mm) | 1-2 |
| Large ulcers (>3 mm) | 3-5 |
| Submucosal infiltration | |
| None | 0 |
| Mild | 1 |
| Moderate | 2-3 |
| Severe | 4-5 |
| Crypt abscesses | |
| None | 0 |
| Rare | 1-2 |
| Diffuse | 3-5 |
| Wall thickness (µm) | |
| <470 | 0 |
| <600 | 1 |
| <700 | 2 |
| <800 | 3 |
| <900 | 4 |
| >900 | 5 |

Results

Anti SR-BI mAb Suppress Long-Term Ongoing EAE

Three groups of mice models of EAE displaying similar clinical manifestations were subjected to monoclonal antibody therapy and control treatments. As shown in FIG. 9, mice treated with PBS or control IgG continued to develop severe EAE, while those treated with the anti SR-BI mAb E12 went into fast remission without residual sign of disease (FIG. 9).

On day 19, spleen cells were isolated from representative mice of each group and cultured for 72 h with the target antigen with which disease was induced. Levels of IL-10, IL-12 (p40 subunit) and IL-4 were then recorded using commercially available ELISA kits. FIGS. 10a-c summarize the results of this experiment showing a marked elevation in IL-10 production (p<0.001), a significant elevation in IL-4 production (p<0.01) accompanied by a significant reduction in IL-12 production (p<0.01). These results are consistent with the in vitro properties of this antibody (see FIGS. 10a-c and may explain, at least in part the beneficial effect of this therapy (FIG. 9).

Spinal cord (lumbar spinal cord) sections obtained on day 19 from control EAE mice and from those subjected to IgG1 or E12 therapy (see FIG. 9) were subjected to an immunohistological analysis of the expression of SR-BI on leukocytes around high endothelial venules (HEV). FIGS. 11a-c show representative sections of untreated control EAE mice, EAE mice treated with E12 and EAE mice treated with control IgG1, respectively. In all sections of sick mice leukocytes entering the CNS highly expressed SR-BI. The reduction in the density of these cells in anti SR-BI treated mice could be explained, in part, by the reduced number of invading leukocytes resulting from the decrease in the inflammatory process (i.e. lower histological score).

Finally representative sections from these groups were subjected to immunohistological analysis of IL-10, using a commercially available anti IL-10 mAb. FIGS. 11d-f show representative sections of untreated control EAE mice, EAE mice treated with E12 and EAE mice treated with control IgG1, respectively. The elevation in IL-10 production in sections of mice treated with E12 is apparent compared to each of the control groups. These results support the above in-vitro results, substantiating the anti-inflammatory role of anti SR-B1 therapy.

Anti SR-BI mAb Suppresses Experimental Colitis

Similar analysis of the effect of anti-SR-B1 monoclonal antibodies on IBD was effected on a rat model of colitis. The following summarizes macroscopic and microscopic analyses on colitis induced rats (6 rats per group), as well as representative samples of histopathological analysis, followed by immunohistochemistry detection of ED1 positive cells (macrophages), CD3+ T cells and IL-10 staining in all groups.

Table 4 below clearly shows that a significant reduction in macroscopic and microscopic scores of disease which is accompanied by a marked reduction in histopathological changes in the colon.

TABLE 4

|  | TNBS | TNBS control IgG | TNBS E12mAb |
|---|---|---|---|
| Mean macroscopic assessment | 4 ± 0.66 | 4.2 ± 0.66 | 2.66 ± 0.5* |
| Mean microscopic assessment | 15 ± 2 | 17.5 ± 2.2 | 6.5 ± 2** |

*$p < 0.01$,
**$p < 0.001$

FIGS. 12a-e show representative histological colon sections obtained at day 12 of IBD onset from naïve rats (FIG. 12a), positive control rats suffering form TNBS induced IBD (FIG. 12b), rats suffering from TNBS induced IBD that were subjected to repeated administration of isotype matched control IgG (FIG. 12c) in comparison to those treated with mAb E12 (FIGS. 12d-e). As shown structural changes between E12 treated colon and control are evident. This may be explained by the shift in cytokine profile from pro-inflammatory (in control treated animals) to anti-inflammatory cytokines (in E12 treated animals) as shown in FIGS. 13a-i.

FIGS. 13a-c show sections of untreated IBD induced rats. Massive submucosal infiltration of macrophages (ED1+) and both mucosal and submucosal infiltration of T cells (CD3+) are shown. IL-10 production was barely detected, mainly in the mucosa.

FIGS. 13d-f show sections of isotype matching control treated animals. Submucosal infiltration of macrophages (ED1+), mucosal infiltration of T cells (CD3+) and minor IL-10 production in the mucosa are detected.

FIGS. 13g-i show sections of E12 treated rats. Submucosal infiltration of macrophages (ED1+) in damaged areas is shown, and presence of macrophages in the lamina propria of unaffected areas is detected. CD3+ T cell infiltrate healthy mucosa, with marked IL-10 production at the mucosa.

REFERENCES CITED

Additional References are Cited in the Text

1. Brown M S, Goldstein J L. Lipoprotein metabolism in the macrophage: implications for cholesterol deposition in atherosclerosis. Annu Rev Biochem 1983; 52:223-61.
2. Krieger M. The other side of scavenger receptors: pattern recognition for host defense. Curr Opin Lipidol 1997; 8:275-80.
3. Krieger M, Herz J. Structures and functions of multiligand lipoprotein receptors: macrophage scavenger receptors and LDL receptor-related protein (LRP). Annu Rev Biochem 1994; 63:601-37.
4. Platt N, Gordon S. Is the class A macrophage scavenger receptor (SR-A) multifunctional?—The mouse's tale. J Clin Invest 2001; 108:649-54.
5. Janeway C A. Approaching the asymptote? Evolution and revolution in immunology. Cold Spring Harb. Symp. Quant. Biol. 1989; 54:1-13.
6. Acton S L, Scherer P E, Lodish H F, Krieger M. Expression cloning of SR-BI, a CD36-related class B scavenger receptor. J Biol Chem 1994; 269:21003-9.
7. Krieger M. Scavenger receptor class B type I is a multiligand HDL receptor that influences diverse physiologic systems. J Clin Invest 2001; 108:793-7.
8. Hyka N, Dayer J M, Modoux C, et al. Apolipoprotein A-I inhibits the production of interleukin-1β and tumor necrosis factor-α by blocking contact-mediated activation of monocytes by T lymphocytes. Blood 2001; 97:2381-9.
9. Youssef S, Maor G, Wildbaum G, Grabie N, Gour-Lavie A, Karin N. C—C chemokine-encoding DNA vaccines enhance breakdown of tolerance to their gene products and treat ongoing adjuvant arthritis. J Clin Invest 2000; 106: 361-71.
10. Youssef S, Wildbaum G, Maor G, et al. Long-lasting protective immunity to experimental autoimmune encephalomyelitis following vaccination with naked DNA encoding C—C chemokines. J Immunol 1998; 161:3870-9.
11. Wildbaum G, Netzer N, Karin N. Plasmid DNA encoding IFN-γ-inducible protein 10 redirects antigen-specific T cell polarization and suppresses experimental autoimmune encephalomyelitis. J Immunol 2002; 168:5885-92.
12. Wildbaum G, Westermann J, Maor G, Karin N. A targeted DNA vaccine encoding fas ligand defines its dual role in the regulation of experimental autoimmune encephalomyelitis. J Clin Invest 2000; 106:671-9.
13. Wildbaum G, Youssef S, Karin N. A targeted DNA vaccine augments the natural immune response to self TNF-α and suppresses ongoing adjuvant arthritis. J Immunol 2000; 165:5860-6.
14. Wildbaum G, Karin N. Augmentation of natural immunity to a pro-inflammatory cytokine (TNF-α) by targeted DNA vaccine confers long-lasting resistance to experimental autoimmune encephalomyelitis. Gene Ther 1999; 6:1128-38.
15. Salomon I, Netzer N, Wildbaum G, Schif-Zuck S, Maor G, Karin N. Targeting the Function of IFN-γ-Inducible Protein 10 Suppresses Ongoing Adjuvant Arthritis. J Immunol 2002; 169:2685-93.
16. Sato Y, Roman M, Tighe H, et al. Immunostimulatoey DNA sequences necessary for effective intradermal gene immunization. Science 1996; 273:352-357.
17. Raz E, Tighe H, Sato Y, et al. Preferential induction of a Th1 immune response and inhibition of specific IgE antibody formation by plasmid DNA immunization. Proc Natl Acad Sci USA 1996; 93:5141-5.
18. Hemmi H, Takeuchi O, Kawai T, et al. A Toll-like receptor recognizes bacterial DNA. Nature 2000; 408:740-5.
19. Wen-Ming C, Xing Gong K, Zhi-Wei L, et al. DNA-PKcs Is Required for Activation of Innate Immunity by Immunostimulatory DNA. Cell 2000; 103:909-918.
20. Mendel I, Kerlero de Rosbo N, Ben-Nun A. A myelin oligodendrocyte glycoprotein peptide induces typical chronic experimental autoimmune encephalomyelitis in H-2b mice: fine specificity and T cell receptor V 13 expression of encephalitogenic T cells. European Journal of Immunology 1995; 25:1951-9.
21. Yednock T A, Cannon C, Fritz L C, Sanchez-Madrid F, Steinman L, Karin N. Prevention of experimental autoimmune encephalomyelitis by antibodies against α4β1 integrin. Nature 1992; 356:63-6.

22. Wildbaum G, Netzer N, Karin N. Tr1 cell-dependent active tolerance blunts the pathogenic effects of determinant spreading. J Clin Invest 2002; 110:701-10.
23. Husemann J, Silverstein S C. Expression of scavenger receptor class B, type I, by astrocytes and vascular smooth muscle cells in normal adult mouse and human brain and in Alzheimer's disease brain. Am J Pathol 2001; 158:825-32.
24. McRae B L, Kennedy M K, Tan L J, Dal Canto M C, Picha K S, Miller S D. Induction of active and adoptive relapsing experimental autoimmune encephalomyelitis (EAE) using an encephalitogenic epitope of proteolipid protein. Journal of Neuroimmunology 1992; 38:229-40.
25. Karin N, Binah O, Grabie N, et al. Short peptide-based tolerogens without self-antigenic or pathogenic activity reverse autoimmune disease. J Immunol 1998; 160:5188-94.

What is claimed is:

1. A method of diagnosing Inflammatory Bowel Disease (IBD) in a human subject, the method comprising:
   (a) contacting a serum sample obtained from the subject with an SR-B1 antigen so as to form immune complexes with human anti-SR-B1 auto-antibodies in said sample,
   (b) detecting anti-SR-B1 immune complexes in said serum sample, and
   (c) determining the level of anti SR-B1 auto-antibodies in said serum sample, wherein an anti-SR-B1 auto-antibody level above a predetermined threshold of said human anti SR-B1 auto-antibodies in said serum sample is indicative of the IBD in the subject.

2. The method of claim 1, wherein detecting said anti SR-B1 auto-antibodies in said serum sample is effected by ELISA, RIA and/or dot blot.

3. The method of claim 1, wherein said serum sample is an immunoglobulin-purified serum sample.

4. The method of claim 1, wherein said predetermined threshold is the level of said anti-SR-B1 antibodies in a serum sample obtained from healthy individuals.

5. The method of claim 1, wherein said SR-B1 antigen is an immobilized SR-B1 antigen.

6. A method of monitoring progression of Inflammatory Bowel Disease (IBD) in a subject suffering from IBD, the method comprising:
   (a) contacting a serum sample obtained from the subject with an SR-B1 antigen so as to form immune complexes with human anti-SR-B1 auto-antibodies in said sample,
   (b) detecting anti-SR-B1 immune complexes in said serum sample, and
   (c) determining the level of anti SR-B1 auto-antibodies in said serum sample from the immune complexes,
   wherein a reduction in anti-SR-B1 auto-antibody level below previously determined serum anti-SR-B1 auto-antibody levels from said subject is indicative of reduced severity of the IBD in the subject.

7. The method of claim 6, wherein said SR-B1 antigen is an immobilized SR-B1 antigen.

8. The method of claim 6, wherein said subject is being treated for IBD.

* * * * *